US006589531B1

(12) United States Patent
Andino-Pavlovsky et al.

(10) Patent No.: US 6,589,531 B1
(45) Date of Patent: Jul. 8, 2003

(54) RECOMBINANT YELLOW FEVER VIRUS AND METHOD OF USE THEREOF

(75) Inventors: Raul Andino-Pavlovsky, San Francisco, CA (US); Andres McAllister-Moreno, Geneva (CH)

(73) Assignee: The Regents of the University of California, Oakland, CA (US)

( * ) Notice: Subject to any disclaimer, the term of this patent is extended or adjusted under 35 U.S.C. 154(b) by 34 days.

(21) Appl. No.: 09/653,754

(22) Filed: Sep. 1, 2000

Related U.S. Application Data

(60) Provisional application No. 60/177,449, filed on Jan. 21, 2000.

(51) Int. Cl.$^7$ .............................................. A61K 39/12
(52) U.S. Cl. ................................ 424/199.1; 424/186.1; 435/69.3; 435/320.1; 514/44
(58) Field of Search ....................... 514/44; 424/186.1, 424/199.1; 435/69.3, 320.1

(56) References Cited

U.S. PATENT DOCUMENTS 5,965,124 A    10/1999  Feinberg et al.
6,184,024 B1 * 2/2001  Lai et al. ................. 435/235.1

FOREIGN PATENT DOCUMENTS

| WO | WO 9306214 | 4/1993 |
|----|------------|--------|
| WO | WO 9700322 | 1/1997 |
| WO | WO 9837911 | 9/1998 |
| WO | WO 9928487 | 6/1999 |

OTHER PUBLICATIONS

Galler et al., The yellow fever 17D vaccine virus: molecular basis of viral attenuation and its use as an expression vector. Brazilian Journal of Medical and Biological Research 30(2):157–168, 1997.*

Monath et al., Recombinant live, attenuated vaccine (ChimeriVax™ incorporating the envelope genes of Japanese encephalitis (SA14–14–2) virus and the capsid and nonstructural genes of yellow fever (17D) virus . . . Vaccine 17:1869–1882, 1999.*

Bonaldo, Myrna C. et al., "The yellow fever 17D vaccine virus as a vector for the expression of foreign proteins: expression of foreign proteins: Development of new live flavivirus vaccines," *Memorias do Instituto Oswaldo Cruz*, vol. 95:suppl. 1, pp. 215–223 (2000).

Guirakhoo, F. et al., "Recombinant chimeric yellow fever–dengue type 2 virus is immunogenic and protective in nonhuman primates," *Journal of Virology*, vol. 74:12, pp. 5477–5485 (2000).

McAllister, Andres et al., "Recombinant yellow fever viruses are effective theraputic vaccines for treatment of murine experimental solid tumors and pulmonary metastases," *Journal of Virology*, vol. 74:19, pp. 9197–9205 (2000).

Monath, T.P. et al., "Chimeric yellow fever virus 17D–Japanese encephalitis virus vaccine: Dose–response effectiveness and extended safety testing in rhesus monkeys," *Journal of Virology*, vol. 74:4, pp. 1742–1751 (2000).

(List continued on next page.)

*Primary Examiner*—Donna C Wortman
(74) *Attorney, Agent, or Firm*—Paula A. Borden; Bozicevic, Field & Francis, LLP

(57) ABSTRACT

The present invention provides recombinant yellow fever viruses (YFV), particularly live attenuated recombinant YFV, which comprise exogenous (i.e., non-YFV) nucleotide sequences which encode exogenous (i.e., non-YFV) amino acid sequences. These recombinant YFV viruses comprise an exogenous nucleic acid. Infection of a host cell with a recombinant YFV provides for expression of the exogenous nucleic acid in a host cell and production of an antigenic polypeptide encoded by the exogenous nucleic acid. Such recombinant YFV are useful in eliciting an immune response to the exogenous polypeptide.

23 Claims, 21 Drawing Sheets

OTHER PUBLICATIONS

Alexander et al. (1994) "Strategies for Inducing and Evaluating Mucosal Immunity: Dicistronic Polioviruses as Expression Vectors for Foreign Genes." *AIDS Research and Human Retroviruses*, vol. 10(2):S57–S60.

Amberger et al (1994) "Characterization of a Membrane-bound Metalloendoprotease of Rat C6 Glioblastoma Cells." *Cancer Research*, vol. 54:4017–4025.

Andino et al. (1994) "Engineering Poliovirus as a Vaccine Vector for the Expression of a Diverse Antigens." *Science*, vol. 265:1448–1451.

Bohm et al. (1998) "T Cell–Mediated, IFN–γ–Facilitated Rejection of Murine B16 melanomas." *The Journal of Immunology*, vol. 161(2):897–908.

Boon (1993) "Tumor Antigens Recognized by Cytolytic T Lymphocytes: Present Perspectives for Specific Immunotherapy." *Int. J. Cancer*, vol. 54:177–180.

Boon et al. (1992) "Identification of Tumour Rejection Antigens Recognized by T Lymphocytes." *Cancer Surveys*, vol. 13:23–37.

Burke et al. (1991) "Antigen Chimeras of Poliovirus." *Prog. Med. Virol.*, vol. 38:56–68.

Carroll et al. (1997) "Highly attenuated modified vaccinia virus Ankara (MVA) as an effective recombinant vector: a Murine tumor model." *Vaccine*, vol. 15(4):387–394.

Chambers et al. (1991) "Processing of the Yellow Fever Virus Nonstructural Polyprotein: a Catalytically Active NS3 Proteinase Domain and NS2B Are Required for Cleavages at Dibasic Sites." *Journal of Virology*, vol. 73(4):3095–3101.

Chambers et al. (1999) "Yellow Fever/Japanese Encephalitis Chimeric Viruses: Construction and Biological Properties." *Journal of Virology*, vol. 73(4):3095–3101.

Chambers et al. (1990) "Evidence that the N–terminal domain of nonstructural protein NS3 from yellow fever virus is a serine protease responsible for site–specific cleavages in the viral polyprotein." *Proc. Natl. Acad. Sci USA*, vol. 87:8898–8902.

Chen et al. (1996) "Therapeutic Antitumor Response After Immunization with a Recombinant Adenovirus Encoding a Model Tumor–Associated Antigen." *The Journal of Immunology*, vol. 156(1):224–231.

de Zoeten et al. (1998) "Resistance to Melanoma in Mice Immunized with Semiallogeneic Fibroblasts Transfected with DNA from Mouse Melanoma Cells." *The Journal of Immunology*, vol. 160(6):2915–2922.

Dranoff et al. (1993) "Vaccination with irradiated tumor cells engineered to secrete murine granulocyte–macrohage colony–stimulating factor stimulates potent, specific, and long–lasting anti–tumor immunity." *Proc. Natl. Acad. Sci. USA*, vol. 90:3539–3543.

Dranoff et al. (1997) "A Phase I Study of Vaccination with Autologous, Irradiated Melanoma Cells Engineered to Secrete Human Granulocyte–Macrophage Colony Stimulating Factor." *Human Gene Therapy*, vol. 7:111–123.

Ellem et al. (1997) "A case report: Immune responses and clinical course of the first human use of granulocyte/macrophage–colony–stimulating–factor–transduced autologous melanoma cells for immunotherapy." *Cancer Immunol Immunother.*, vol. 44:10–20.

Falo et al. (1995) "Targeting antigen into the phagocytic pathway in vivo induces protective tumour immunity." *Nature Medicine*, vol. 1(7):649–653.

Guirakhoo et al. (1999) "Immunogenicity, genetic Stability and Protective Efficacy of a Recombinant, Chimeric Yellow Fever–Japanese Encephalitis Virus (ChimeriVax–JE) as a Live, Attenuated Vaccine Candidate against Japanese Encephalitis." *Virology*, vol. 257:363–372.

Kawakami et al. (1994) "Identification of a human melanoma antigen recognized by tumor–infiltrating lymphocytes associated with in vivo tumor rejection." *Proc. Natl. Acad. Sci. USA*, vol. 91:6458–6462.

Kawakami et al. (1994) "Identification of the Immunodominant Peptides of the MART–1 Human Melanoma Antigen Recognized by the Majority of HLA–A2–restricted Tumor Infiltrating Lymphocytes." *The Journal of Experimental Medicine*, Vol. 180:347–352.

Kawakami et al, (1994) "Cloning of the gene coding for a shared human melanoma antigen recognized by autologous T cells infiltrating into tumor." *Proc. Natl. Acad. Sci. USA*, vol. 91:3515–3519.

Khromykh et al. (1997) "Subgenomic Replicons of the Flavivirus Kunjin: Contruction and applications." *Journal of Virology*, vol. 71(2):1497–1505.

Lu et al. (1995) "Construction and Genetic Analysis of Dicistronic Polioviruses Containing Open Reading Frames for Epitopes of Human Immunodeficiency Virus Type 1 gp120." *Journal of Virology*, vol. 69(8):4797–4806.

Mandl et al. (1998) "Poliovirus vaccine vectors elicit antigen–specific cytotoxic t cells and protect mice against lethal challenge with malignant melanoma cells expressing a model antigen." *Proc. Natl. Acad. Sci. USA*, vol. 95:8216–8221.

Monath (1991) "Yellow Fever: Victor, Victoria? Conqueror, conquest? Epidemics and research in the last forty years and prospects for the future." *Am. J. Trop. Med. Hyg.*, vol. 45(1):1–43.

Monath et al. (1993) "Should Yellow Fever Vaccine be Included in the Expanded Program of Immunization in Africa? A Cost–Effectiveness Analysis for Nigeria." *Am. J. Trop. Med. Hyg.*, vol. 48(2):274–299.

Monath et al. (1999) "Recombinant, chimaeric live, attenuated vaccine (ChimeriVax™) incorporating the envelope genes of Japanese encephalitis (SA144–2) virus and the capsid and nonstructural genes of yellow fever (17D) virus is safe, immunogenic and protective in non–human primates." *Vaccine*, vol. 17:1869–1882.

Monath (1990) Flaviviruses. In *Virology*, G.N. Fields, and D.M. Knipe, eds. Raven Press, Ltd., New York. pp. 763–814.

Mueller et al. (1998) "Expression of Foreign Proteins by Poliovirus Polyprotein Fusion: Analysis of genetic Stability Reveals Rapid deletions and Formation of Cardioviruslike Open Reading Frames." *Journal of Virology*, vol. 72(1):20–31.

Overwijk et al. (1999) "Vaccination with a recombinant vaccinia virus encoding a "self" antigen induces autoimmune vitiligo and tumor cell destruction in mice: Requirement for CD4+ T lymphocytes." *Proc. Natl. Acad. Sci. USA*, vol. 96:2982–2987.

Poland et al. (1981) "Persistence of neutralizing antibody 30–35 years after immunization with 17D yellow fever vaccine." *Bulletin of the World Health Organization*, vol. 59(6):895–900.

Reinhardt et al. (1998) "Development of Viremia and Humoral and Cellular Parameters of Immune Activation After Vaccination With Yellow Fever Virus Strain 17D: A Model of Human Flavivirus Infection." *Journal of Medical virology*, vol. 56:159–167.

Restifo et al., (1996) "The new vaccines: building viruses that elicit antitumor immunity." *Curr. Opin. Immunol.*, vol. 8:658–663.

Rice et al., (1989) "Transcription of Infectious Yellow Fever RNA From Full–Length cDNA Templates Produced by In Vitro Ligation." *The New Biologist*, vol. 1(3):285–296.

Rooney et al. (1988) "Immunization with a Vaccinia Virus Recombinant Expressing Herpes Simplex Virus Type 1 Glycoprotein D: Long–Term Protection and Effect of Revaccination." *Journal of Virology*, vol. 62(5):1530–1534.

Rosenberg et al. (1994) "Treatment of Patients with Metastatic Melanoma with Autologous Tumor–Infiltrating Lymphocytes and Interleukin 2." *Journal of the National Cancer Institute*, vol. 86(15):1159–1166.

Rotzschke et al. (1990) "Isolation and analysis of naturally processed viral peptides as recognized by cytotoxic T cells." *Nature*, vol. 348:252–254.

Simons et al. (1997) "Bioactivity of Autologous Irradiated Renal Cell Carcinoma Vaccines Generated by ex Vivo Granulocyte–Macrophage Colony–stimulating Factor Gene Transfer." *Cancer Research*, vol. 57:1537–1546.

Tang et al. (1997) "Poliovirus RNA recombination.'" *RNA*, vol. 3:624–633.

Varnavski et al. (1999) "Noncytopathic Flavivirus Replicon RNA–Based System for Expression and Delivery of Heterologous Genes." *Virology*, vol. 255:366–375.

Westaway (1987) "Flavivirus Replication Strategy." *Advances in Virus Research*, vol. 33:45–90.

Xie et al., (1998) "Yellow Fever 17D vaccine virus isolated from healthy vaccines accumulates very few mutations." *Virus research*, vol. 55:93–99.

Yang et al. (1997) "Immunotherapeutic Potential of Tumor Antigen–Pulsed and Unpulsed Dendritic Cells Generated from Murine Bone Marrow." *Cellular Immunology*, vol. 179:84–95.

"Fatal Viral Encephalitis Following 17D Yellow Fever Vaccine Inoculation." *JAMA*, vol. 198(6):203–204.

GenBank Accession No. X03700 K02749, deposited Feb. 17, 1997.

* cited by examiner

FIG. 1

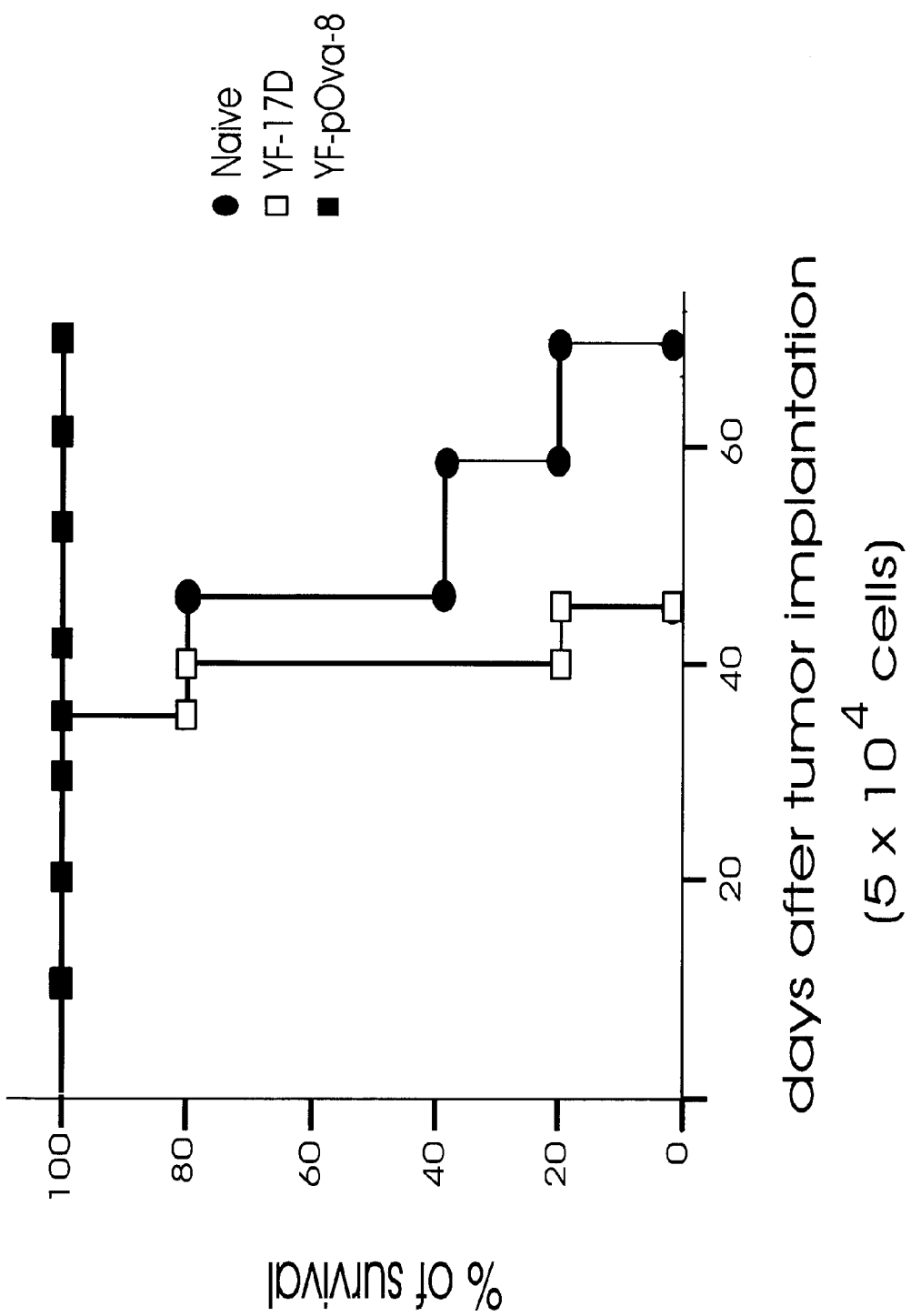

RECOMBINANT YELLOW FEVER VIRUS AND METHOD OF USE THEREOF

CROSS-REFERENCE TO RELATED APPLICATIONS

This application claims the benefit of U.S. Provisional Application No. 60/177,449, filed Jan. 21, 2000, which application is incorporated herein by reference.

GOVERNMENT RIGHTS

The United States Government may have certain rights in this application pursuant to U.S. Public Health Service grant A144343.

FIELD OF THE INVENTION

The invention relates generally to the field of recombinant viruses and induction of specific immunity, specifically to induction of tumor-specific immunity.

BACKGROUND OF THE INVENTION

Tumor-specific cytotoxic T lymphocytes (CTLs) can prevent or eradicate tumors in a number of experimental systems and in patients with cancer (1–3). Clinical trials have demonstrated that 35% of patients with melanoma treated with specific, tumor-reactive lymphocytes can achieve either partial or complete tumor regression (4). The antigens recognized by the T cells have, in some cases, been identified (5, 6). Although cancer cells may express tumor-associated antigens (TAAs), CTLs directed against TAAs are not efficiently elicited by the growing tumor and, therefore, the immune system fails to control tumor growth. Thus, it appears that tumor cells lack either immunogenicity and/or the appropriate co-stimulation required for CTL activation.

In contrast to tumor cells, viruses are strong inducers of cellular immune responses. Thus, activation of the tumor-directed CTL response by vaccination with recombinant viruses expressing tumor-associated antigens is a promising approach for the prevention and treatment of malignancies. Viral vaccine vectors that have been successfully used in experimental cancer models include poxviruses, adenoviruses, picornaviruses and influenza viruses (7–10). However, because each vaccine vector may present its own set of beneficial and adverse properties, the search for new vectors continues to be an active area of research. For example, clinical use of some vectors currently under study may be limited by their record of safety, efficacy, potential oncogenicity or induction of immunosuppression. In addition, preexisting immunity against the vector could hinder the potency of treatment (8, 11), and therefore alternative viral vectors are needed.

There is a need in the field for viral vectors that can be used to induce immunity to a wide variety of antigens, including those present on tumors. The present invention addresses this need, and provides related advantages as well.

SUMMARY OF THE INVENTION

The present invention provides recombinant yellow fever viruses (YFV), particularly live attenuated recombinant YFV, which comprise exogenous (i.e., non-YFV) nucleotide sequences which encode exogenous (i.e., non-YFV) amino acid sequences. These recombinant YFV viruses comprise an exogenous nucleic acid. Infection of a host cell with a recombinant YFV provides for expression of the exogenous nucleic acid in a host cell and production of an antigenic polypeptide encoded by the exogenous nucleic acid. Such recombinant YFV are useful in eliciting an immune response to the exogenous polypeptide.

The recombinant live attenuated YFV express an exogenous nucleotide sequence which encodes an exogenous polypeptide, such as, but not limited to, a polypeptide obtained from a pathogenic agent other than YFV, a tumor antigen, and the like. These recombinant YFV are useful, when introduced into a mammalian subject, in eliciting an immune response to the exogenous polypeptide in the subject. Thus, the recombinant YFV of the invention serve as immunization vehicles.

A wide variety of antigenic amino acid sequences can be incorporated into the YFV polyprotein, including those of microbial pathogens (e.g., bacteria, parasites, viruses (other than YFV), fungi, and the like) and tumor-associated antigens. In general, following infection of a host cell by the recombinant virus of the invention, the exogenous polypeptide is proteolytically cleaved from the viral polyprotein precursor into which it is incorporated. The exogenous polypeptide may then be exported to the host cell surface, may be presented on the cell surface as a peptide with a major histocompatibility antigen, may be secreted from the cell, or may remain in the cytoplasm of the cell. In the context of tumor immunotherapy, expression of a exogenous polypeptide in a host elicits an immune response to the tumor, with the result that the tumor cell mass and/or tumor cell number is reduced, development of a tumor is prevented or delayed, and/or the probability that a tumor will develop is reduced.

The invention provides pharmaceutical compositions comprising recombinant YFV of the invention. Such compositions can be used, for example, to reduce the severity of disease, reduce the risk of clinical disease, prevent the onset of a disease and/or to ameliorate the disease via recruitment of the host immune system.

The invention also provides methods of eliciting an immune response to an antigen in a mammalian subject. Such methods comprise administering a recombinant YFV of the invention to a mammalian subject so as to elicit an immune response to the exogenous polypeptide. The antigen can be a host antigen or an antigen of a non-YFV pathogen.

The invention further provides methods of reducing or inhibiting tumor cell growth, and methods of reducing tumor cell mass and/or tumor cell numbers. Such methods comprise administering a recombinant YFV of the invention which comprises exogenous sequences encoding a tumor-associated antigen (TAA)/epitope to a host bearing a tumor, such that the recombinant YFV enters a cell of the host and the exogenous TAA polypeptide is expressed on the surface of a host cell, is presented in the context of an MHC molecule, or, alternatively, secreted from the host cell. An immune response is elicited to a tumor which bears on its surface an antigen which comprises the exogenous TAA polypeptide or which resembles the exogenous polypeptide sufficiently to elicit an immune response toward the tumor cell. The immune response to the tumor bearing the tumor-associated antigen on its surface is sufficient to reduce, inhibit, or eliminate the tumor.

The invention further provides methods of preventing tumor cell growth, and methods of reducing the probability that a tumor will form, comprising administering a recombinant YFV of the invention, which comprises a tumor-associated antigen/epitope-encoding nucleic acid, to a host not bearing a tumor, such that the recombinant YFV enters a host cell, the tumor-associated antigen is expressed on the host cell surface and/or presented in the context of an MHC molecule (e.g., MHC Class 1), and an immune response is elicited to the tumor-associated antigen. The immune response to the tumor-associated antigen is sufficient to prevent, or reduce the likelihood, of tumor development in the host.

A primary object of the invention is to provide a recombinant YFV that provides for production of an exogenous polypeptide that is suitable for induction of an immune response to the polypeptide in a host following infection with the recombinant YFV. Such exogenous polypeptides include, but are not limited to, an antigen produced by the host (e.g., a tumor antigen), or an antigen from a non-YFV pathogen (e.g., a retroviral antigen).

An advantage of the invention is that the recombinant YFV of the invention are live attenuated virus, which will continue to propagate until the intervention of the host's immune system.

Another advantage of the invention is that the YFV exhibits low toxicity in vivo.

Yet another advantage of the invention is that the YFV can express a polypeptide inside the host cell, and thus can provide for induction of an immune response, particularly a cellular immune response that involves, for example, antigen-specific cytotoxic T lymphocytes (CTLs).

Yet another advantage of the invention is that the immune response elicited using the YFV of the invention is not limited to the infected cells, as the immune system will also recognize cells ea ring the antigen expressed by the recombinant YFV. For example, the production of a tumor antigen by the recombinant YFV can "break immune tolerance" to tumor antigens, and induce an immune response against the tumor effective to, for example, inhibit tumor growth.

These and other objects, advantages, and features of the invention will become apparent to those persons skilled in the art upon reading the details of the invention as more fully described below.

BRIEF DESCRIPTION OF THE DRAWINGS

FIG. 1 is a schematic diagram of a yellow fever virus vector, YF-pOva, and strategy for expression of chicken ovalbumin. The top bar represents YF Vector genomic RNA. Boxes-below represent mature viral- proteins. White arrows indicate NS2B/NS3 cleavage sites, black triangles indicate cellular signal peptidase cleavage sites. Nucleotide sequences encoding the ovalbumin $K^b$ epitope SIINFEKL and flanking viral protease cleavage were inserted at the N-terminus or at the junctions between C-prM and NS2B-NS3 (indicated by black arrows).

FIGS. 4A–D: Local tumor growth. The size of the tumor was determined every five days and is plotted as the average tumor area +/− standard deviation in square $cm^2$ vs. time post-challenge (days). FIGS. 5A–D: Survival is plotted as the percentage of surviving animals vs. time. All experiments included 10 mice per group and were repeated three times.

FIGS. 9A and 9B depict survival plotted as the percentage of surviving animals vs. time following implantation of $5 \times 10^4$ cells (FIG. 9A) or $1 \times 10^6$ cells (FIG. 9B). All experiments included 10 mice per group. Naive: closed circles; YF-17D, open squares; YF-pOva-8, closed squares.

DETAILED DESCRIPTION OF PREFERRED EMBODIMENTS

Figure 2:
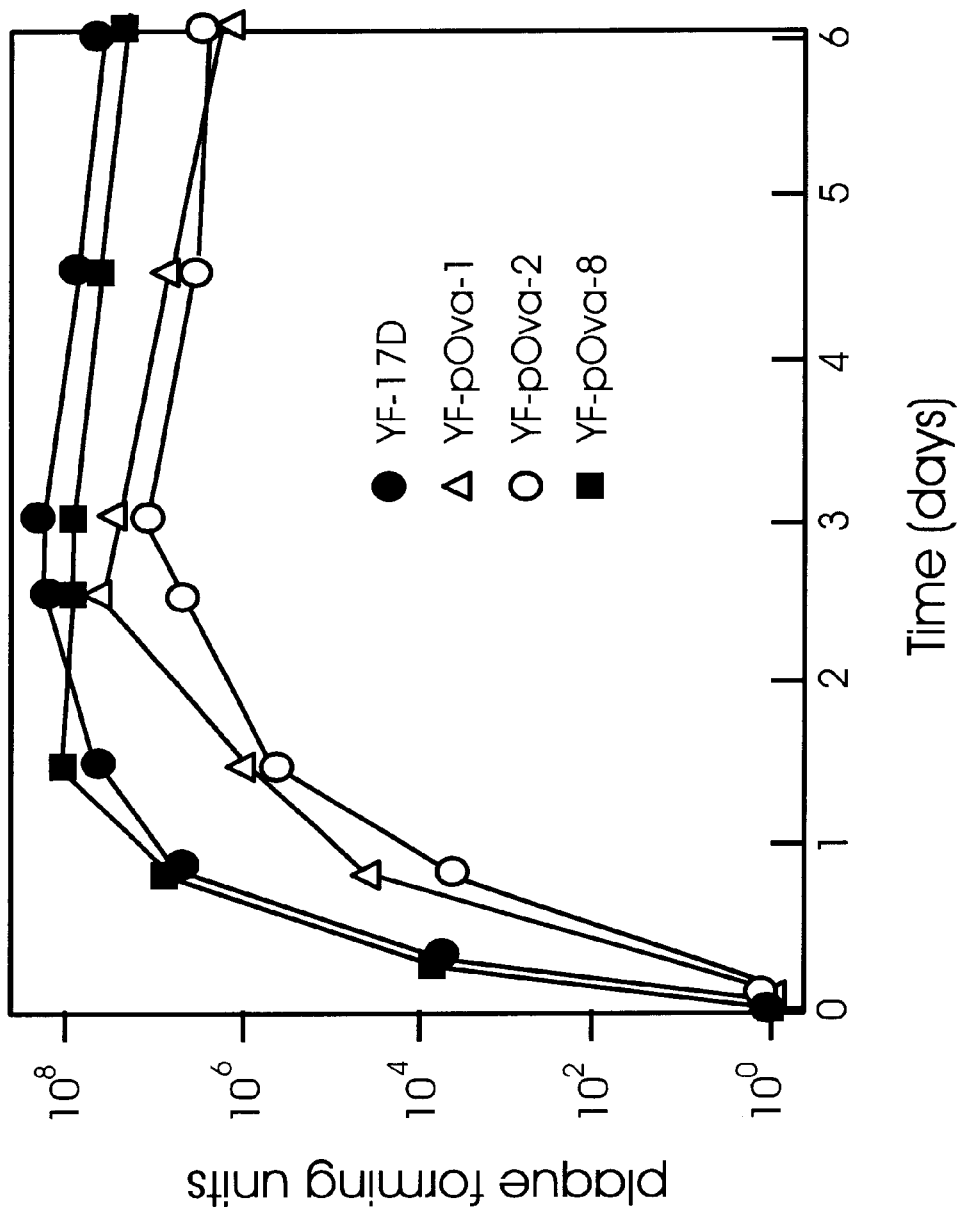
FIG. 2 depicts one-step growth curves of parental yellow fever 17D strain (YF-17D) and three YF virus vectors: YF-pOva-1 (open triangles), YF-pOva-2 (open circles), and YF-pOva-8 (closed squares). SW13 cell monolayers were infected (MOI=5) with YF-17D, YF-pOva-1, YF-pOva-2, or YF-pOva-8. Virus production (pfu/ml) was determined at each time point by plaque assay.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a recombinant virus"

includes a plurality of such viruses and reference to "the epitope" includes reference to one or more epitopes and equivalents thereof known to those skilled in the art, and so forth.

The publications discussed herein are provided solely for their disclosure prior to the filing ate of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "polynucleotide" and "nucleic acid", used interchangeably herein, refer to a polymeric forms of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "oligopeptide," "polypeptide," "polyprotein," and "protein", are used interchangeably herein, and refer to a polymeric form of amino acids of any length, which can include coded and non-coded amino acids, chemically or biochemically modified or derivatized amino acids, and polypeptides having modified peptide backbones.

"Recombinant," as used herein, means that a particular DNA sequence is the product of various combinations of cloning, restriction, and/or ligation steps resulting in a construct having a structural coding sequence distinguishable from homologous sequences found in natural systems. Generally, DNA sequences encoding the structural coding sequence can be assembled from cDNA fragments and short oligonucleotide linkers, or from a series of oligonucleotides, to provide a synthetic gene which is capable of being expressed in a recombinant transcriptional unit. Such sequences can be provided in the form of an open reading frame uninterrupted by internal nontranslated sequences, or introns, which are typically present in eukaryotic genes. Genomic DNA comprising the relevant sequences could also be used. Sequences of non-translated DNA may be present 5' or 3' from the open reading frame, where such sequences do not interfere with manipulation or expression of the coding regions. Thus, e.g., the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

By "construct" is meant a recombinant nucleic acid, generally recombinant DNA, that has been generated for the purpose of the expression of a specific nucleotide sequence(s), or is to be used in the construction of other recombinant nucleotide sequences.

Similarly, a "recombinant polypeptide" or "recombinant polyprotein" refers to a polypeptide or polyprotein which is not naturally occurring, or is made by the artificial combination of two otherwise separated segments of amino acid sequences. This artificial combination may be accomplished by standard techniques of recombinant DNA technology, such as described above, i.e., a recombinant polypeptide or recombinant polyprotein may be encoded by a recombinant polynucleotide. Thus, a recombinant polypeptide or recombinant polyprotein is an amino acid sequence encoded by all or a portion of a recombinant polynucleotide.

The term "immunologically active" or "immunogenic" refers to the capability of the natural, recombinant, or synthetic peptide to induce a specific humoral and/or cellular immune response in a mammal. As used herein, "antigenic amino acid sequence," "antigenic polypeptide," or "antigenic peptide" means an amino acid sequence that, either alone or in association with an accessory molecule (e.g., a class I or class II major histocompatibility antigen molecule), can elicit an immune response in a mammal.

As used herein, "an immune response" is meant to encompass cellular and/or humoral immune responses that are sufficient to inhibit or prevent infection, or prevent or inhibit onset of disease symptoms caused by a microbial organism, particularly a pathogenic microbial organism, and/or to inhibit, reduce, or prevent proliferation of a tumor cell, and/or to reduce tumor cell numbers or tumor mass, and/or to reduce the likelihood that a tumor will form.

The term "tumor-associated antigen" is a term well understood in the art, and refers to surface molecules that are differentially expressed in tumor cells relative to non-cancerous cells of the same cell type. As used herein, "tumor-associated antigen" includes not only complete tumor-associated antigens, but also epitope-comprising portions (fragments) thereof. A tumor-associated antigen (TAA) may be one found in nature, or may be a synthetic version of a TAA found in nature, or may be a variant of a naturally-occurring TAA, e.g., a variant has enhanced immunogenic properties.

The terms "antigen" and "epitope" are well understood in the art and refer to the portion of a macromolecule which is specifically recognized by a component of the immune system, e.g., an antibody or a T-cell antigen receptor. Epitopes are recognized by antibodies in solution, e.g., free from other molecules. Epitopes are recognized by T-cell antigen receptor when the epitope is associated with a class I or class II major histocompatibility complex molecule.

As used herein the term "isolated" is meant to describe a compound of interest (e.g., a virus, a peptide, etc.) that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, preferably 75% free, and most preferably 90% free from other components with which it is naturally associated.

By "subject" or "individual" or "patient," which terms are used interchangeably herein, is meant any subject, particularly a mammalian subject, for whom diagnosis or therapy is desired, particularly humans. Other subjects may include cattle, dogs, cats, guinea pigs, rabbits, rats, mice, horses, and so on. Of particular interest are those subjects susceptible to infection by yellow fever virus, e.g., subjects who can support YFV replication.

A "biological sample" encompasses a variety of sample types obtained from an organism and can be used in a diagnostic or monitoring assay. The term encompasses blood and other liquid samples of biological origin, solid tissue samples, such as a biopsy specimen or tissue cultures or cells derived therefrom and the progeny thereof. The term encompasses samples that have been manipulated in any way after their procurement, such as by treatment with reagents, solubilization, or enrichment for certain components. The term encompasses a clinical sample, and also includes cells in cell culture, cell supernatants, cell lysates, serum, plasma, biological fluids and tissue samples.

The terms "treatment," "treating," and the like are used herein to generally refer to obtaining a desired pharmacologic or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, e.g., a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease. In some embodiments, the invention is directed toward treating patients with cancer. In these embodiments, "treatment" can include reducing or inhibiting tumor cell growth, eliminating a tumor, reducing metastasis, reducing or inhibiting tumor cell proliferation, reducing tumor cell mass, reducing tumor cell number, and reducing the probability that a tumor will form.

The terms "cancer", "neoplasm", "tumor", and "carcinoma", are used interchangeably herein to refer to cells which exhibit relatively autonomous growth, so that they exhibit an aberrant growth phenotype characterized by a significant loss of control of cell proliferation. Cancerous cells can be benign or malignant.

Recombinant Yellow Fever Virus The present invention provides recombinant yellow fever viruses (YFV), particularly live attenuated recombinant YFV, which comprise exogenous ( i.e., non-YFV) nucleotide sequences which encode exogenous (i.e., non-YFV) amino acid sequences. Such recombinant YFV are useful in eliciting an immune response to the exogenous peptide. For simplicity, "exogenous" is used throughout as exemplary of such sequences, but is not intended to be limiting.

Yellow fever virus is an enveloped, positive-stranded RNA virus and a member of the flaviviridae genus. The genome is approximately 11 kb in length and encodes a single polypeptide (16). This polypeptide precursor is proteolytically processed during and after translation, generating the functional proteins necessary for viral replication. Processing is mediated by cellular and viral proteases that recognize short specific amino acid sequences present at the junctions of the viral proteins. The viral protease NS2B/NS3 mediates most of the cleavages of the non-structural proteins in the cytosol of the infected cell (17–19).

The encoded exogenous polypeptide is expressed in the context of normal viral protein translation, preferably as a component of a recombinant or fusion precursor polypeptide. The recombinant polyprotein generally comprises the exogenous polypeptide and viral polypeptide, and preferably further comprises an artificial proteolytic recognition site or sites. The proteolytic recognition site(s) can be positioned in recombinant precursor polypeptide so that the precursor polyprotein is proteolytically processed by viral or cellular protease(s) so as to release the free exogenous protein from the viral proteins.

The starting YFV, which is subsequently modified to include the exogenous sequences, is referred to as the "parent" YFV, which can be a native yellow fever virus (either pathogenic or, preferably, non-pathogenic), an attenuated yellow fever virus, a vaccine yellow fever virus strain or a recombinant yellow fever virus. Any of a variety of strains of YFV can be used in generating recombinant YFV as described herein. The nucleotide sequence of a number of YFV strains are available in public databases, including, e.g., GenBank. An exemplary strain is "YFV 17D." The nucleotide sequence of the YFV genome, as well as the amino acid sequence of the encoded viral polyprotein are found under GenBank Accession No. X03700, and are also described in Rice et al. ((1985) Science 229:726–733), both of which are incorporated herein by reference in their entirety for the nucleotide and protein sequences disclosed therein. Production of yellow fever virions (viral particles) is well known in the art.

In general, an exogenous nucleic acid(s) inserted into the YFV genome comprises a nucleotide sequence encoding an exogenous polypeptide (i.e., non-YFV polypeptide) and at least one nucleotide sequence encoding a proteolytic cleavage site. The nucleotide sequence encoding the exogenous polypeptide may be flanked on either side by nucleotide sequences encoding proteolytic cleavage sites. Alternatively, the nucleotide sequence encoding the exogenous polypeptide may be flanked on only one side by a nucleotide sequence encoding a proteolytic cleavage site. In the latter case, the insertion site may be chosen such that, after insertion, the nucleotide sequence encoding the exogenous polypeptide is flanked on either side by nucleotide sequences encoding proteolytic cleavage sites, one of which was present in the parent YFV genome immediately adjacent the site of insertion. The exogenous nucleic acid sequence encoding the exogenous polypeptide and the nucleic acid sequence encoding the proteolytic cleavage sites can be positioned various sites within the YFV genome. As non-limiting examples, the exogenous nucleic acid sequence may be inserted at one or more of the following locations: (1) the N-terminus of the viral polypeptide; (2) between viral proteins C and prM; (3) between viral proteins NS2A and NS2B; (4) between viral proteins NS2B and NS3; (5) between viral proteins NS3 and NS4A; and (5) NS4A and NS4B. The exogenous nucleic acid can be inserted at other sites in the YFV genome. Preferably, insertion of the exogenous nucleic acid does not disrupt YFV protein function, and/or proteolytic processing of the viral polypeptide, and/or viral replication. Whether viral replication is adversely affected can be determined using well-established techniques, including, but not limited to, a plaque assay, and a one-step growth curve assay, as described in Example 1.

Unlike other vectors which will produce only one cycle of antigen expression and/or which will stop expression without the intervention of the host immune system, the active recombinant virus of the invention will continue to propagate until the immune system is sufficiently activated to halt the infection. This produces a stronger immune response against the exogenous antigenic peptide produced from the YFV as compared to the immune response that would be elicited using conventional expression vectors (e.g., a viral replicon).

The recombinant YFV also exhibits low toxicity to a host upon infection. For example, YF-17D is a very safe and effective live viral vaccine, prepared from infected chicken embryos under standards developed by the World Health Organization. After vaccination, immunity is elicited within 10 days in over 95% of vaccines (12) and neutralizing antibodies directed against the virus can be detected for more than 35 years (13). The vaccine safety record is outstanding: serious adverse reactions to YF-17D vaccine are extremely uncommon, and reversion to wild type is virtually non-existent (14, 15).

Additional features may be incorporated into the design of replication-competent recombinant YFV viruses, such as polylinker sequences (e.g., EcoR1, Not1, BssH2, and Xho1) to facilitate the ease of insertion of desired foreign sequences into the recombinant vector. Also, variants, such as a poly-glycine tract, may be inserted adjacent to the inserted sequence so as to enhance the structural flexibility of the region and potentially increase the efficiency of proteolytic processing.

More than one nucleic acid sequence encoding an exogenous protein or polypeptide to be produced can be included in the recombinant replication-competent YFV virus which, as a result, produces the corresponding number of exogenous proteins or polypeptides. The two or more nucleic acid sequences can each encode a different product or can encode the same product (e.g., if enhanced production of a protein or polypeptide is desired).

Insertion of exogenous nucleic acid can be accomplished by standard techniques of molecular biology, such as described in numerous standard protocol texts, including e.g., *Current Protocols in Molecular Biology*, (F. M. Ausubel, et al., Eds. 1987, and updates. Example 1 provides further guidance for how particular insertions were accomplished. Using these guidelines, any of a variety of exogenous nucleic acids can be inserted into the YFV genome:

The exogenous nucleic acid can be from about 12 to about 18, from about 15 to about 24, from about 21 to about 30, from about 30 to about 60, from about 60 to about 90, from about 90 to about 120, from about 120 to about 150, from about 150 to about 180, from about 180 to about 240, from about 240 to about 300, from about 300 to about 600, from about 600 to about 1200, from about 1200 to about 1500, from about 1500 to about 2100, from about 2100 to about 2400, from about 2400 to about 3000 nucleotides in length.

Recombinant YFV as described herein can be used to induce an immune response against an antigen in an individual and, e.g., provide protection against challenge or infection by the exogenous pathogen (bacterial, viral, fungal, parasitic) in which the antigen occurs. They are, therefore, useful as vaccines to provide immune protection against such pathogens.

Any DNA sequence which encodes a polypeptide or protein which, when expressed, produces protective immunity against, for example, a pathogenic organism or against a condition or disorder associated with the presence of or caused by an antigen, can be considered exogenous nucleic acids for the purpose of the present invention. Nucleic acid sequences encoding one or more exogenous polypeptides (e.g., antigens or epitopes) of interest can be included in a vaccine of the present invention. If more than one exogenous antigen or epitope of interest is encoded by the exogenous nucleic acid sequences, they can be antigens or epitopes of a single pathogen or antigens or epitopes from more than one (different). In a preferred embodiment, such an organism is a pathogenic microorganism. For example, such an exogenous epitope may be found on bacteria, parasites, viruses or fungi which are the causative agents of diseases or disorders. In addition, epitopes of allergens, sperm and cancer cells can be used. Thus, in some embodiments, where more than one exogenous peptide is encoded by the exogenous nucleic acid sequences, the more than one exogenous peptide can be different epitopes found on a single TAA.

The exogenous proteins in the vaccine formulations of the invention can also comprise an epitope of an exogenous organism. When the exogenous polypeptide is expressed in a vertebrate host, it elicits an immune response that protects against a condition or disorder caused by or associated with expression of or the presence in the host of, an antigen comprising the epitope. For example, in this embodiment of the invention, exogenous proteins that comprise an epitope (s) or protein(s) of snake venom, bee venom, a hormone, sperm (for contraception), an allergy-inducing antigen or any other antigen to which an immune response is desired, may be used. In another embodiment, a tumor-specific antigen can be expressed as a recombinant exogenous protein, for induction of a protective, or otherwise therapeutic, immune response against cancer.

The gene sequences encoding the exogenous protein to be expressed by the recombinant virus according to the present invention, can be obtained by techniques known in the art, including but not limited to, chemical or enzymatic synthesis, purification from genomic DNA of the microorganism, by purification or isolation from a cDNA encoding a TAA, by cDNA synthesis from RNA of the microorganism, or by recombinant DNA methods (Maniatis et al., Molecular Cloning, A Laboratory Manual, 1982, Cold Spring Harbor Laboratory, Cold Spring Harbor, N.Y.).

When they are used as vaccines, the recombinant YFV of the present invention are administered to an individual using known methods. They will generally be administered by the same routes by which conventional (presently-available) vaccines are administered and/or by routes which mimic the route by which infection by the pathogen of interest occurs. They can be administered in a vaccine composition which includes, in addition to the replication-competent recombinant virus, a physiologically acceptable carrier. The composition may also include an immunostimulating agent or adjuvant, flavoring agent, or stabilizer.

Conventional and pharmaceutically acceptable routes of administration include intranasal, intramuscular, intratracheal, intratumoral, subcutaneous, intradermal, intravenous, rectal, nasal, oral and other parenteral routes of administration. Routes of administration may be combined, if desired, or adjusted depending upon the antigenic peptide or the disease. The vaccine composition can be administered in a single dose or in multiple doses, and may encompass administration of booster doses, to elicit and/or maintain immunity.

The recombinant YFV vaccine is administered in an "effective amount," that is, an amount of recombinant YFV that is effective in a selected route of administration to elicit an immune response effective to facilitate protection of the host against infection, or symptoms associated with infection, by a pathogenic organism. In some embodiments, an "effective amount" of a recombinant YFV vaccine is an amount of recombinant YFV that is effective in a route of administration to elicit an immune response effective to reduce or inhibit tumor cell growth, to reduce tumor cell mass or tumor cell numbers, or to reduce the likelihood that a tumor will form.

The amount of recombinant YFV in each vaccine dose is selected as an amount which induces an immunoprotective or other immunotherapeutic response without significant, adverse side effects generally associated with typical vaccines. Such amount will vary depending upon which specific immunogen is employed, whether or not the vaccine formulation comprises an adjuvant, and a variety of host-dependent factors. In general, it is expected that each dose of vaccine will be sufficient to generate, upon infection of host cells, about 1–1000 µg of protein, generally from about 1–200 µg, normally from about 10–100 µg. An effective dose of recombinant YFV nucleic acid-based vaccine will generally involve administration of from about 1–1000 µg of nucleic acid. An optimal amount for a particular vaccine can be ascertained by standard studies involving observation of antibody titers and other responses in subjects. The levels of immunity provided by the vaccine can be monitored to determine the need, if any, for boosters. Following an assessment of antibody titers in the serum, optional booster immunizations may be desired. The immune response to the protein of this invention is enhanced by the use of adjuvant and or an immunostimulant.

Recombinant YFV viruses of the present can also be used as a system for producing the exogenous polypeptide in host cells, such as mammalian, particularly human, cells or other cell types. The exogenous protein is then isolated using standard methods.

In either application (i.e., immunization or tissue culture production) the exogenous nucleic acid sequence introduced into the YFV can be one obtained from a source in which it occurs naturally, produced using genetic engineering methods or synthesized chemically or enzymatically. The exogenous nucleic acid sequence introduced into the virus can encode an entire antigen against which an immune response is desired or antigenic epitopes or portions, e.g., an immunogenic fragment of from about 4 to about 1000, from about 10 to about 500, from about 15 to about 250, from about 20 to about 100, from about 25 to about 50 amino acids. Inserted sequences are expected to present to the host immune system, antigenic structures defined both by primary sequence and structural conformation.

Compositions comprising recombinant Yellow Fever Viruses of the invention

The present invention further provides compositions, including pharmaceutical compositions, comprising the recombinant YFV of the invention.

Compositions comprising recombinant YFV of the invention may include a buffer, which is selected according to the desired use of the recombinant YFV, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, "Remington: The Science and Practice of Pharmacy", 19th Ed.. (1995) Mack Publishing Co.

Pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

When used as a vaccine, a recombinant YFV of the invention can be formulated in a variety of ways. In general, the vaccine of the invention is formulated according to methods well known in the art using suitable pharmaceutical carrier(s) and/or vehicle(s). A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a vaccine composition of the invention may be formulated to contain other components, including, e.g., adjuvants, stabilizers, pH adjusters, preservatives and the like. Such components are well known to those of skill in the vaccine art.

Methods of using the recombinant Yellow Fever Viruses of the invention

The present invention provides methods for eliciting an immune response to an antigen, comprising administering a recombinant YFV of the invention to a mammalian subject, wherein the YFV enters a cell, the exogenous polypeptide is released by proteolytic cleavage, and an immune response is elicited to the exogenous polypeptide.

In some embodiments, a polypeptide antigen expressed on a given tumor cell (e.g., a tumor associated antigen; "TAA") is inserted into a recombinant YFV of the invention as described herein. Such recombinant YFV can be administered to an individual having, or suspected of having, a tumor. In some cases, such recombinant YFV can be administered to an individual who does not have a tumor, but in whom protective immunity is desired. As is often the case, the immune system does not mount an immune response effective to inhibit or suppress tumor growth, or eliminate a tumor altogether. Tumor-associated antigens are often poorly immunogenic; perhaps due to an active and ongoing immunosuppression against them. Furthermore, cancer patients tend to be immunosuppressed, and only respond to certain T-dependent antigens. In these cases, introduction into the host of a recombinant YFV of the invention which expresses an exogenous peptide corresponding to an antigen expressed on the tumor cell surface can elicit an immune response to the tumor in the host. As shown in the Examples, a recombinant YFV comprising an insert encoding the sequence SIINFEKL ("Ova") (SEQ ID NO.:1), which is recognized specifically by CD8$^-$ cytotoxic T cells (CTLs) when presented on the surface of a cell together with a class I MHC molecule, was introduced into mice. When mice were subsequently challenged with a tumor expressing Ova on its surface, a robust CTL response was mounted against the tumor.

Any of a variety of known tumor-associated antigens (TAA) can be inserted into YFV of the invention. The entire TAA may be, but need not be, inserted. Instead, a portion of a TAA, e.g., an epitope, may be inserted. Tumor-associated antigens (or epitope-containing fragments thereof) which may be inserted into YFV include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV 18, TUAN, alpha-feto protein (AFP), OFP, CA-125, CA-50, CA-19-9, renal tumor-associated antigen G250, EGP-40 (also known as EPCAM), S100 (malignant melanoma-associated antigen), p53, and p21ras.

Recombinant YFV comprising a TAA can be administered to an individual as described above. Whether an immune response is elicited to a given tumor can be determined by methods standard in the art, including, but not limited to, assaying for the presence and/or amount of TAA-specific antibody in a biological sample derived from the individual, e.g., by enzyme-linked immunosorbent assay (ELISA), radioimmunoassay (RIA), and the like; assaying for the presence and/or numbers of CTLs specific for a TAA; and the like. Examples of how to assay for the presence and/or numbers of TAA-specific CTLs are found in the Examples section herein below. Standard immunological protocols may be used, which can be found in a variety of texts, including, e.g., Current Protocols in Immunology (J. E. Coligan, A. M. Kruisbeek, D. H. Margulies, E. M. Shevach and W. Strober Eds. 1991).

In other embodiments, the exogenous (non-YFV) polypeptide is an antigenic polypeptide of a microbial pathogen. Such recombinant YFV can then be administered to a host to prevent or treat infection by the pathogen, or to prevent or treat symptoms of such pathogenic infection. Of particular interest is the prevention or treatment of infection or disease caused by microbial pathogens that, during the course of infection, are present intracellularly, e.g., viruses (e.g., HIV), bacteria (e.g., Shigella, Listeria, and the like), parasites (e.g., malarial parasites (e.g., Falciparum), trypansomes, and the like), etc. Antigenic polypeptides of such microbial pathogens are well known in the art, and can be readily selected for use in the present recombinant YFV vaccine by the ordinarily skilled artisan.

Whether an immune response is effective can be determined by standard assays, including, but not limited to, measuring tumor cell mass, measuring numbers of tumor cells in an individual, and measuring tumor cell metastasis. Such assays are described in the Examples section herein below.

Using the methods and compositions described herein in connection with the subject invention, an immunoprotective response against microbial infection can be induced in any subject, human or non-human, susceptible to infection by a microbial pathogen. Where the recombinant YFV comprises an exogenous nucleic acid sequence encoding a TAA, the subject may be one that is known to have cancer, is suspected of having cancer, or does not have cancer, but in whom immunity to cancer is to be induced.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Generating Recombinant Yellow Fever Virus

Materials and Methods

Plasmids and PCR fragments. Plasmids pYF5'3' and pYFM5.2 which encode for the complete YFV-17D sequence were kindly provided by Dr. Charles Rice. A full-length viral RNA can be generated from these plasmids by an in vitro ligation procedure (20). Briefly, we inserted a PCR generated DNA fragment, encoding a 13 amino acid peptide from chicken ovalbumin flanked by BssHII and BstEII or ClaI and NdeI restriction enzyme sites, and followed by the viral peptidase (NS2B-NS3 complex) recognition site. We inserted the fragment at the following sites of the viral cDNA: the N-terminus of the viral polypeptide, or between proteins C-prM, NS2A-NS2B, NS2B-NS3, NS3-NS4A and NS4A-NS4B. To insert foreign sequences within the structural region of the genome, PCR fragments containing the foreign sequences were cloned into plasmid p5'3' at each different location. To generate recombinants in the non-structural part of the genome, 8 kb PCR fragments corresponding to the YFV-sequences in pYFM5.2 and containing the inserts of interest were produced. These PCR fragments were used as substitutes for plasmid pYFM5.2 in the in vitro ligation reaction described below.

Generation of Viruses from Plasmids. Production of a molecular clone of YFV-17D was carried out following a similar procedure originally published by Rice and co-workers (20). Briefly, 5 µg of each plasmid (or the corresponding sequences generated by PCR) were digested with restriction enzymes Aat II and Apa I. After digestion, the plasmid containing the 5' and 3' ends of the viral genome and the fragment from YFM5.2 corresponding to the middle region were each purified using low-melting agarose gel electrophoresis and ligated in equimolar concentrations for 4 hours at 16° C. Ligase was inactivated by incubation for 20 minutes at 60° C. The ligated DNA was then digested with Xho I and used as the template for in vitro transcription by SP6 RNA polymerase (Promega, Madison, Wis.) in the presence of $m^7$GpppAmp (New England Biolabs, Beverly, Mass.). Without further purification, synthetic RNA was transfected into BHK-21 cells by electroporation (BTX electro cell manipulator 600, San Diego, Calif.).

Viral Stocks. Cytopathic effect (CPE) was observed 3 to 5 days following transfection. Viruses were cloned from individual plaques produced in BHK-21 cells. To generate viral stocks, cloned viruses were propagated in SW13 cells; supernatants of infected cells were cleared, aliquoted, titered and stored at −70° C.

Single-Step Growth Curves. Subconfluent SW13 cell monolayers were washed once with PBS and infected at a multiplicity of infection of 5 pfu/cell. After a 2 hr incubation period at 37° C., the cells were washed twice with PBS and then covered with L-15 medium supplemented with 10% FCS. Infected cell cultures were incubated at 37° C. for several days, and 100 µl aliquots were recovered every six hours for a period of 6 days or until total CPE occurred. Titers were determined by plaque assay.

Analysis of Viral RNA by RT-PCR. After subsequent passages of recombinant viruses on SW13 cells, total cytoplasmic RNA was obtained from infected cells following the method of (21). Reverse transcription was carried out with Superscript (Gibco-BRL), using random hexamers and specific primer (ATCGCGGACCGAGTGGTTT TGTGTTTGTCATCCAAAGGTCTGCTTATTCT TGAGC (SEQ ID NO.: 2)) and following the manufacturer's recommended protocol. After 1 hour incubation at 42° C., 2 µl of each reaction product was used as template in a PCR reaction using RtTh (Perkin-Elmer) and specific primers flanking the sequence to be studied (CAATGAGGCACTCGCAGCAGCTGG (SEQ ID NO.: 3) and TGCCCTAGCTCTGTGCGCTGCCC YF-pOva-8 (SEQ ID NO.: 4)). The amplified PCR product was analyzed by restriction enzyme digestion and/or DNA sequencing.

Results

Figure 1:
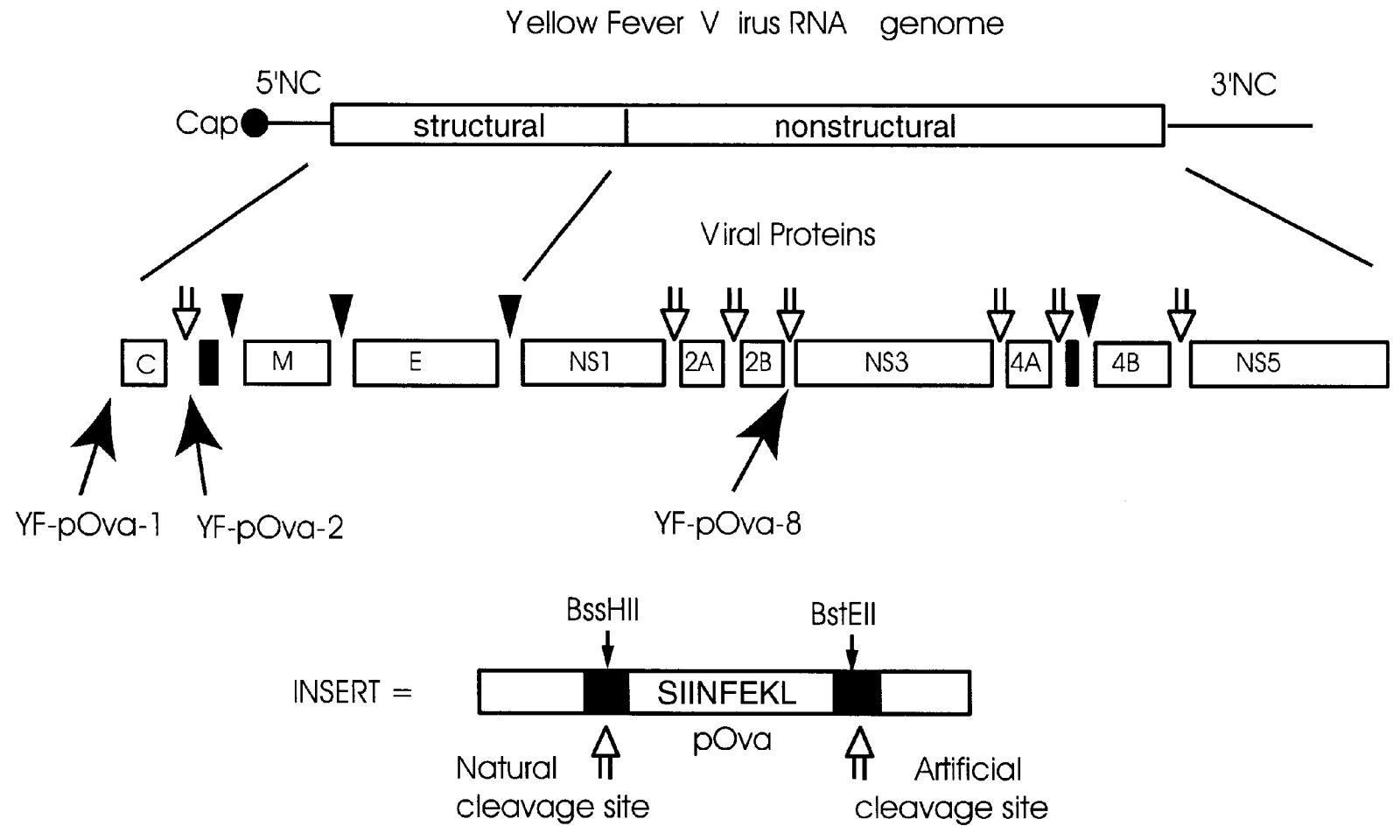

Generation of YFV 17 D recombinants expressing a chicken ovalbumin T-cell epitope. Foreign sequences (flanked by protease recognition sites) are inserted in-frame at different positions within the YF polyprotein precursor. In this way, the viral protease recognizes and cleaves the flanking proteolytic sites, freeing the exogenous antigenic sequences from the rest of the YF polyprotein, and all of the YF proteins are produced correctly and viral replication proceeds normally (FIG. 1). At several positions of the viral genome, we introduced sequences encoding a chicken ovalbumin CTL epitope followed by an eight amino acid cleavage site for the viral protease NS2B/NS3 (FIG. 1). The inserted fragment encoded the amino acid sequence SIINFEKL (SEQ ID NO.: 1), an epitope restricted to the murine MHC class I molecule H-2 $K^b$ (25).

Recombinant live yellow fever viruses were recovered by transfection of BHK cells with in vitro synthesized RNA. Insertion of exogenous sequences at three sites in the genome yielded viable recombinant viruses: the amino terminus, C-prM, and NS2B-NS3 junctions (the resulting viruses were named YF-pOva-1, YF-pOva-2 and YF-pOva-8, respectively). In contrast, insertion at the NS2A-NS2B, NS3-NS4A, NS4A-NS4B junctions abolished viral replication (data not shown). The viruses were isolated from individual plaques and viral stocks were generated by two sequential passages in SW13 cells.

Plaque assays and one-step growth curves showed that recombinants YF-pOva-1, YF-pOva-2 and YF-pOva-8 replicate at rates remarkably similar to the parental 17D strain (FIG. 2). Recombinant YF-pOva-8 replicated with identical kinetic to 17D and achieved nearly equivalent titers. Recombinant YF-pOva-1 and YF-pOva-2 replicated slower than the parental 17D, exhibiting a lag in replication, and by three days post-infection achieved only 10–20% the titer of 17D (FIG. 2). In view of the better replication properties of YF-pOva-8, this recombinant was used in all subsequent studies to further characterize the immunogenicity of yellow fever vectors.

Genetic stability problems have been reported with some positive strand RNA virus vectors (26, 27). Therefore we confirmed the presence of the inserted sequence by RT-PCR and a diagnostic restriction enzyme digest. The original genetic structure of YF-pOva-8 was retained after six passages in BHK-21 cells. Thus, foreign peptides can be introduced between the NS2B and NS3 coding sequences of the yellow fever genome without major compromise of viral replication.

Example 2

Cells Infected with YF-pOva-8 Present the Ovapeptide SIINFEKL in a MHC Class I-restricted Manner Materials and Methods Cell lines. In addition to BHK-21 and SW13 cells already described, the following cell lines were used in the antigen presentation assay or in the tumor rejection challenge: B3Z (T-cell hybridoma), EL-4 (thymoma) and EL4-SL8 cells: B3Z cells and EL4-SL8 were kindly provided by Nilabh Shastri, University of California, Berkeley. EL4-SL8 cells stably express and present the Ova CTL epitope (SIINFEKL (SEQ ID NO.: 1)). B3Z is a murine T cell hybridoma specific for $K^b$ +SIINFEKL (SEQ ID NO.:1), which is transfected with the LacZ-reporter gene under the transcriptional control of the IL-2 enhancer element. Thus, B3Z cell activation can be easily detected by the expression of β-galactosidase (22). The C57BL/6-derived melanoma B16F0 and B16-OVA were a kind gift from Kenneth Rock, University of Massachusetts. B16-Ova (Mo5.20.10) is a cell line that stably expresses ovalbumin constructed by transfection of B16F0 with plasmid pAc-neo-Ova (1).

Antigen Presentation Assay. EL4 cells were mock-infected or infected with YF-17D and recombinant viruses at a MOI of 10 pfu/cell. After a 48 hours incubation period at 37° C., the infected cells or the same number of B16-Ova control cells were co-cultured with $5 \times 10^4$ B3Z cells for 16 hrs at 37° C. To determine the expression of β-galactosidase, cultures were washed with PBS and then fixed with 1% formaldehyde/0.2% glutaraldehyde for 5 min at 4° C. Cells were washed again and incubated with a solution consisting of I mg/ml X-Gal, 5 mM potassium ferrocyanide, 5 mM potassium ferricyanide, and 2 mM $MgCl_2$ in PBS. They were then incubated overnight at 37° C. and examined microscopically for the presence of β-galactosidase activity (blue cells).

Results

Cells infected with YF-pOva-8 present the Ova-peptide SIINFEKL in a MHC class I-restricted manner. To determine whether cells infected with recombinant yellow fever viruses are able to both express and present antigens in an MHC class I-restricted manner, we infected EL4 cells with YF-pOva-8 and co-cultivated the infected cells with a T-cell hybridoma that recognizes SIINFEKL presented in the context of $K^b$ MHC class I molecules. The antigen is initially expressed in the cytoplasm of the infected cell, but it should be transported and presented on the surface of the cell through the MHC class I pathway. We used the T-cell hybridoma B3Z, carrying a lacZ reporter gene under the transcriptional control of the interleukin-2 enhancer element NF-AT (22). Thus, TCR-specific stimulation of B3Z cells can be measured by the production of β-galactosidase activity.

EL4 cells infected with YF-pOva-8 activated 10% of the hybridoma T-cells after 12–16 hours of co-cultivation. In contrast, co-cultivation with uninfected EL4 cells or the hybridoma B3Z by itself did not produce β-galactosidase activity. Co-cultivation with a cell line that stably expresses ovalbumin strongly induced β-galactosidase production. These results demonstrated that polypeptides expressed by yellow fever recombinants are processed and presented in a MHC class I-restricted manner. In addition, western blotting using antibodies directed against viral proteins indicated that all yellow fever virus proteins are correctly produced and processed in YF-pOva-8 infected cells suggesting that the foreign antigen was appropriately cleaved away from the viral polyprotein.

Example 3

Induction of Ova-specific CD8+ T-cells by Recombinant YF-pOva-8

Materials and Methods

CD8+ T cell responses. Immunizations. Groups of 3 C57BL/6 mice were mock infected or immunized i.v. with 10 7 pfu/mouse of either YFV 17D or recombinant virus YF-pOva-8. All groups were boosted i.p. with the same dose at day 21 post infection. Seven days later, all mice were sacrificed and their spleens removed and dispersed to single cell suspensions.

Restimulations and tetramer binding assays. $3 \times 10^6$ splenocytes were restimulated by co-culturing them for 4 days with $10^5$ SIINFEKL-expressing EL4 cells (EL4-SL8) irradiated at 6000 rads. SIINFEKL-MHC class I tetramers were the kind gift of Dr. John Altman (Emory University, Atlanta, Ga.). At day 4, cells were stained as described by Altman et al (23) and analyzed by flow cytometry.

Immunizations and Tumor Challenge. C57BL/6 mice (H-$2^b$) were purchased from the Jackson Laboratory and used between 6–8 weeks of age. Groups of 5 or 10 mice were immunized intraperitoneally (i.p.), subcutaneously (s.c.), intramuscularly (i.m.) or intravenously (i.v.) with $3\times10^5$ pfu/mouse of YF 17D or YF-pOva-8 (Ova-expressing 17D recombinant virus). All groups were boosted with the same dose two weeks later. Non-immunized mice were used as naive controls. Melanoma cells were harvested by incubation in $Ca^{++}$, $Mg^+$ free PBS for 5 minutes, and viable cells counted by trypan blue exclusion and 30 days post infection all mice were challenged with a s.c. injection of $5\times10^4$ B16-OVA or B16F0 melanoma cells. The size of tumors was determined twice a week and expressed as tumor area corresponding to the largest perpendicular diameter in $cm^2$. Animals that developed tumors greater than 2.0 were sacrificed.

Immunotherapy of solid tumors. Mice were injected s.c. with $5\times10^4$ B16-OVA cells. Treatment was started at day 0, 5 or 10 post tumor implantation and consisted of three s.c. injections of $4\times10^5$ pfu YF-pOVA-8 or 17D given in 5 day intervals. A control group was left untreated. Mice were observed for tumor development every 3 days and tumors larger than 0.3 $cm^2$ were scored as positive.

Immunotherapy of experimental pulmonary metastasis. Mice were injected i.v. with either $5\times10^4$ or $1\times10^5$ B16-OVA cells. Immunotherapy was performed as described for solid tumors. On day 30, ten mice of each group were sacrificed, then the lungs were removed, placed for 5 minutes in 3% $H_2O_2$ in $H_2O$, and then fixed in Bouin's solution (Sigma diagnostics, St. Louis, Mo., U.S.A.). The $H_2O_2$ treatment facilitates the analysis of metastasis under the dissecting microscope by inflating the lungs and bleaching hemorrhages which otherwise could be mistaken for metastases.

Results

Figures 3A, 3B, 3C:
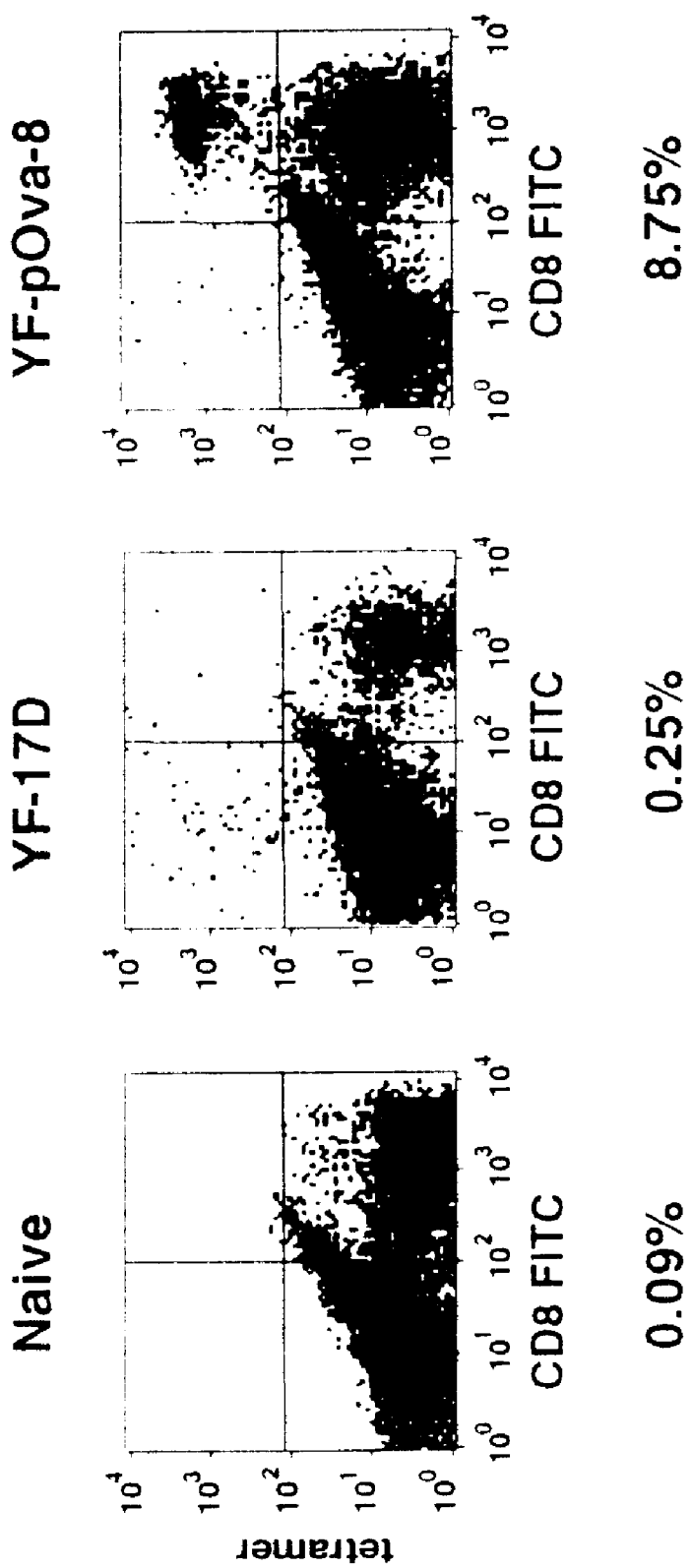
FIGS. 3A–3C depict in vivo activation of CD8+ T cells to Ova peptide. Tetrameric SIINFEKL/murine MHC class I molecule H-2 $K^b$ complex bound to CD8+ splenocytes. Flow cytometry histograms illustrating tetramer binding to gated CD8− T lymphocytes of naive mice or mice infected with parental YF-17D or recombinant YF-pOva-8. Splenocytes were restimulated by co-cultivation for five days with EL4 cells expressing SIINFEKL (EL4-SL8). The values indicate the percentage of CD8+ T lymphocytes that bound the tetramer.
Figure 4A:
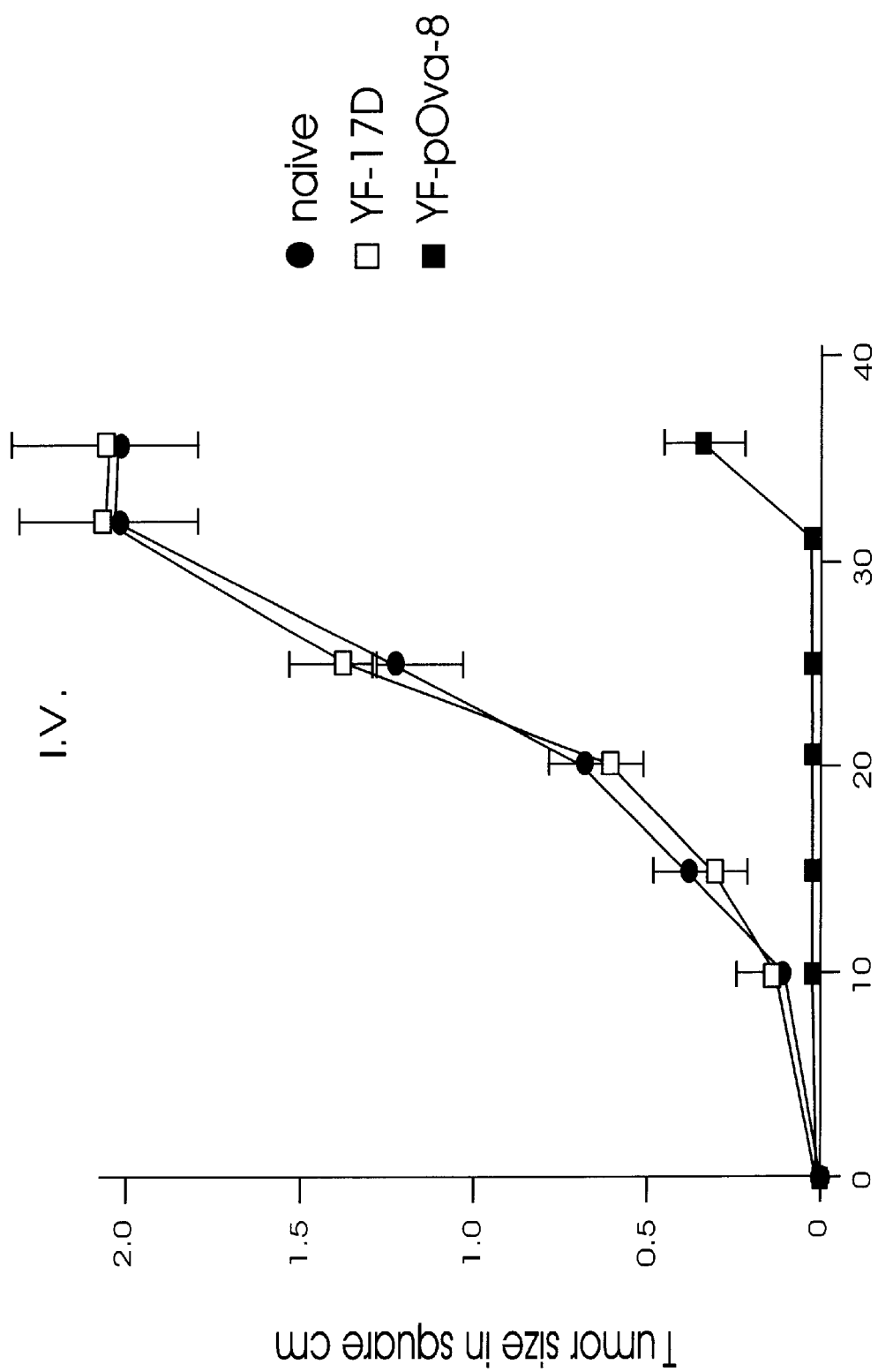
FIGS. 4A–D and 5A–D depict the results of immunization with YF vector, which induces protective and antigen-specific immunity to melanoma B16 expressing Ova. C57BL/6 mice were immunized either twice every 2 weeks intravenously (i.v., FIGS. 4A and 5A), intraperitoneally (i.p., FIGS. 4B and 5B), subcutaneously (s.c., FIGS. 4C and 5C) or intramuscularly (i.m., FIGS. 4D and 5D) with YF-pOva-8 ($3 \times 10^5$ pfu/mouse) (closed squares). As a control, mice were inoculated with either parental YF-17D (open squares) or saline (naive) (closed circles). Thirty days after first immunization (day 0) animals were challenged with $5 \times 10^4$ B16-Ova.
Figure 4B:
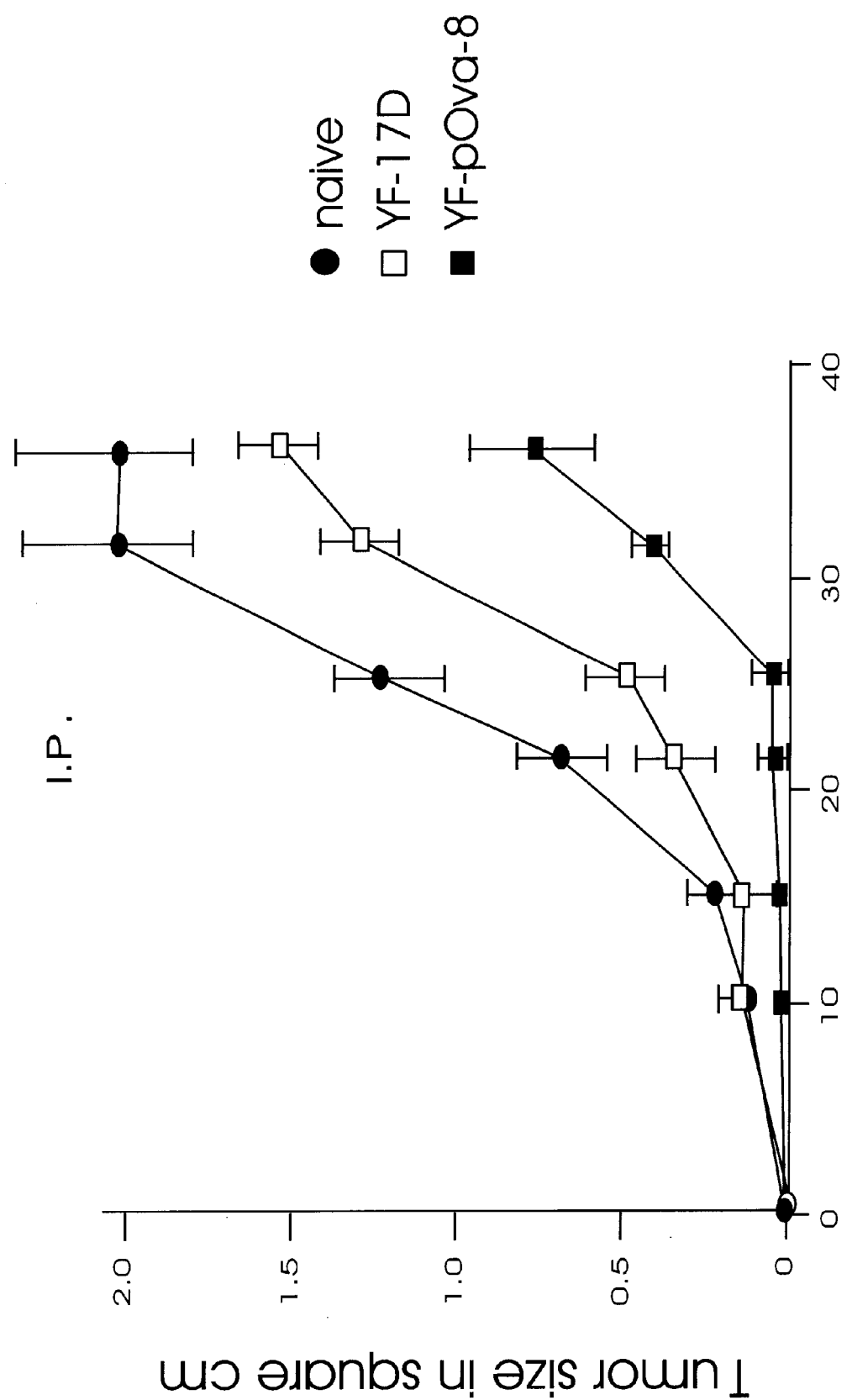
Figure 4C:
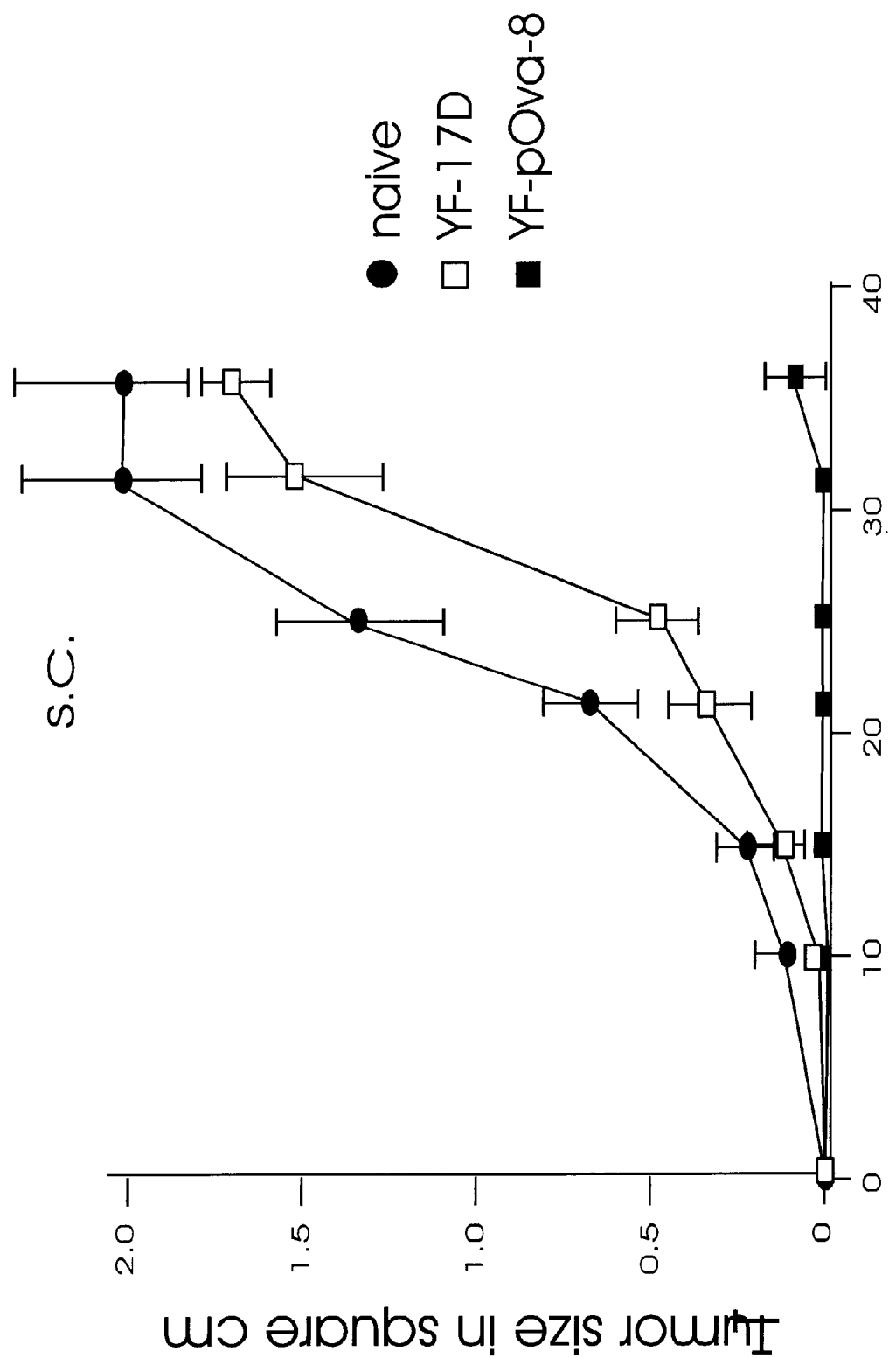
Figure 4D:
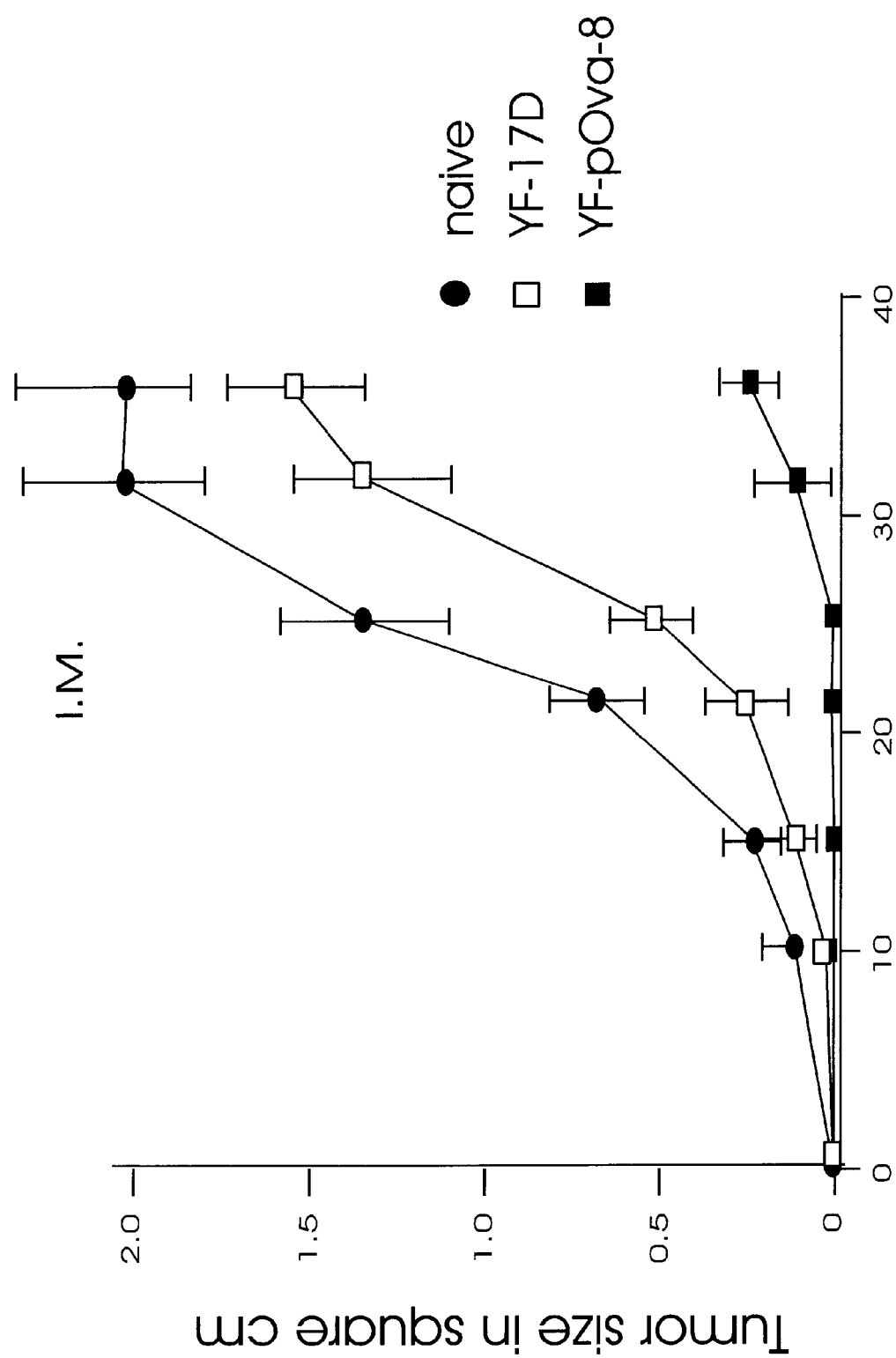
Figure 5A:
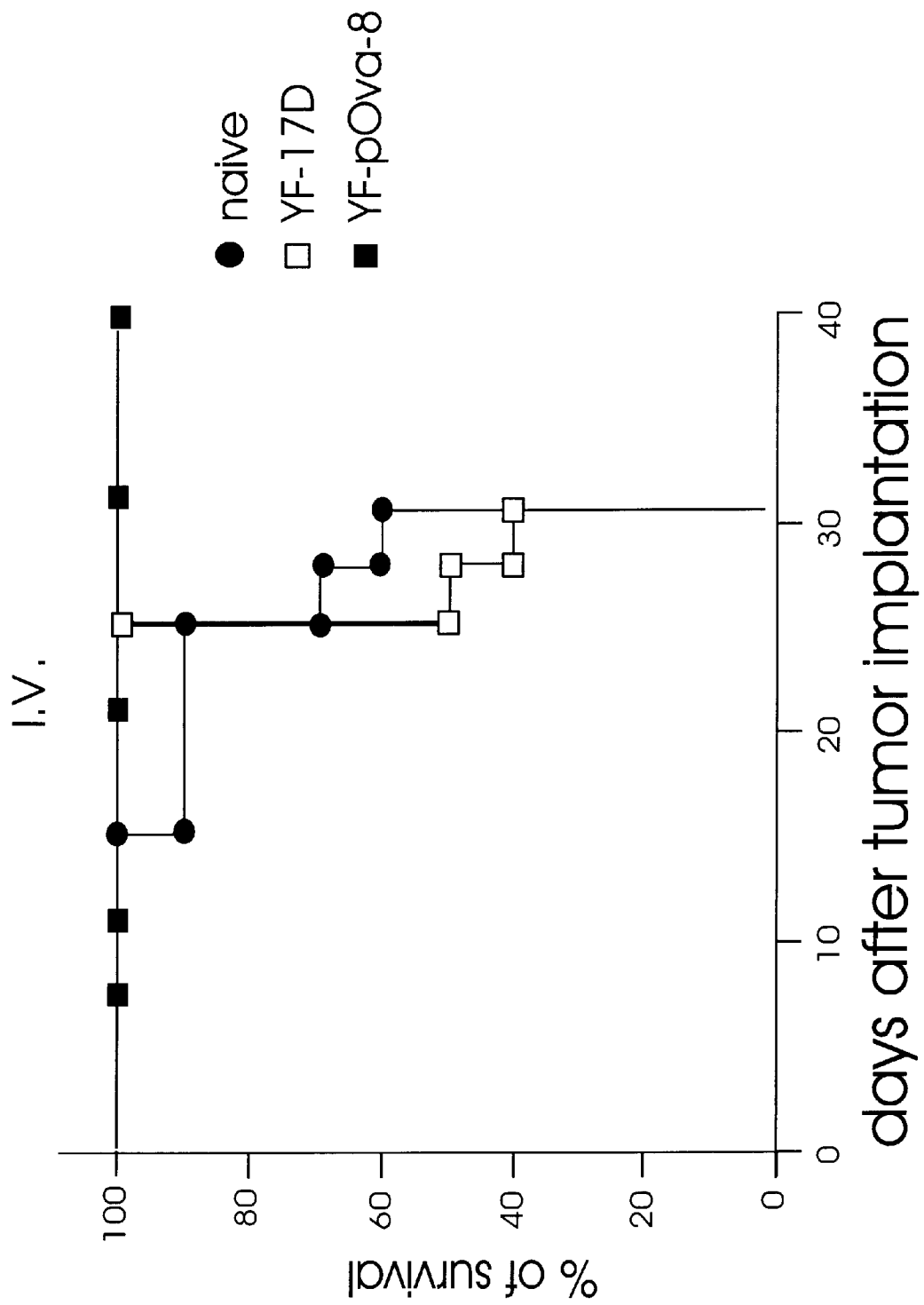
Figure 5B:
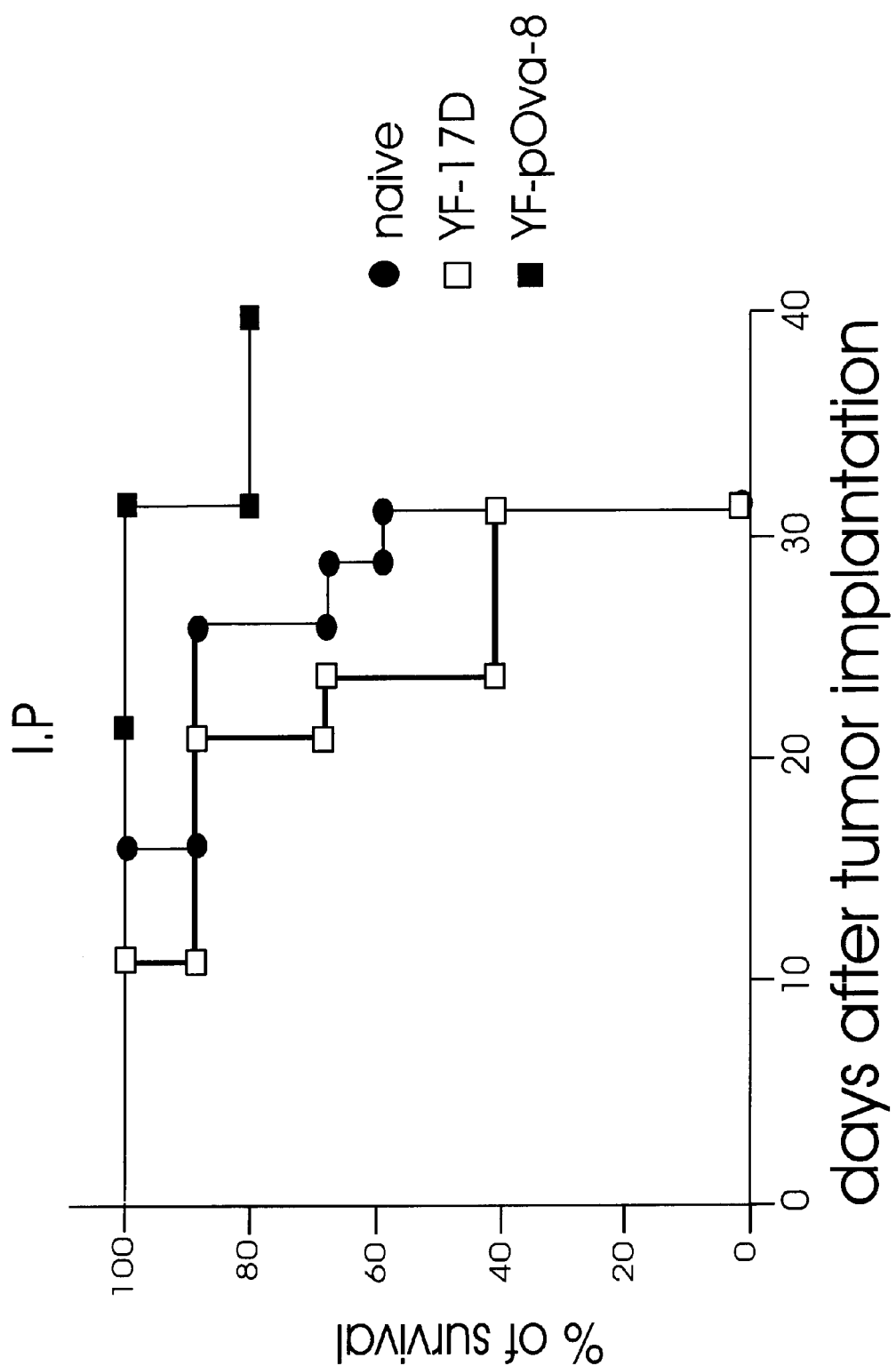
Figure 5C:
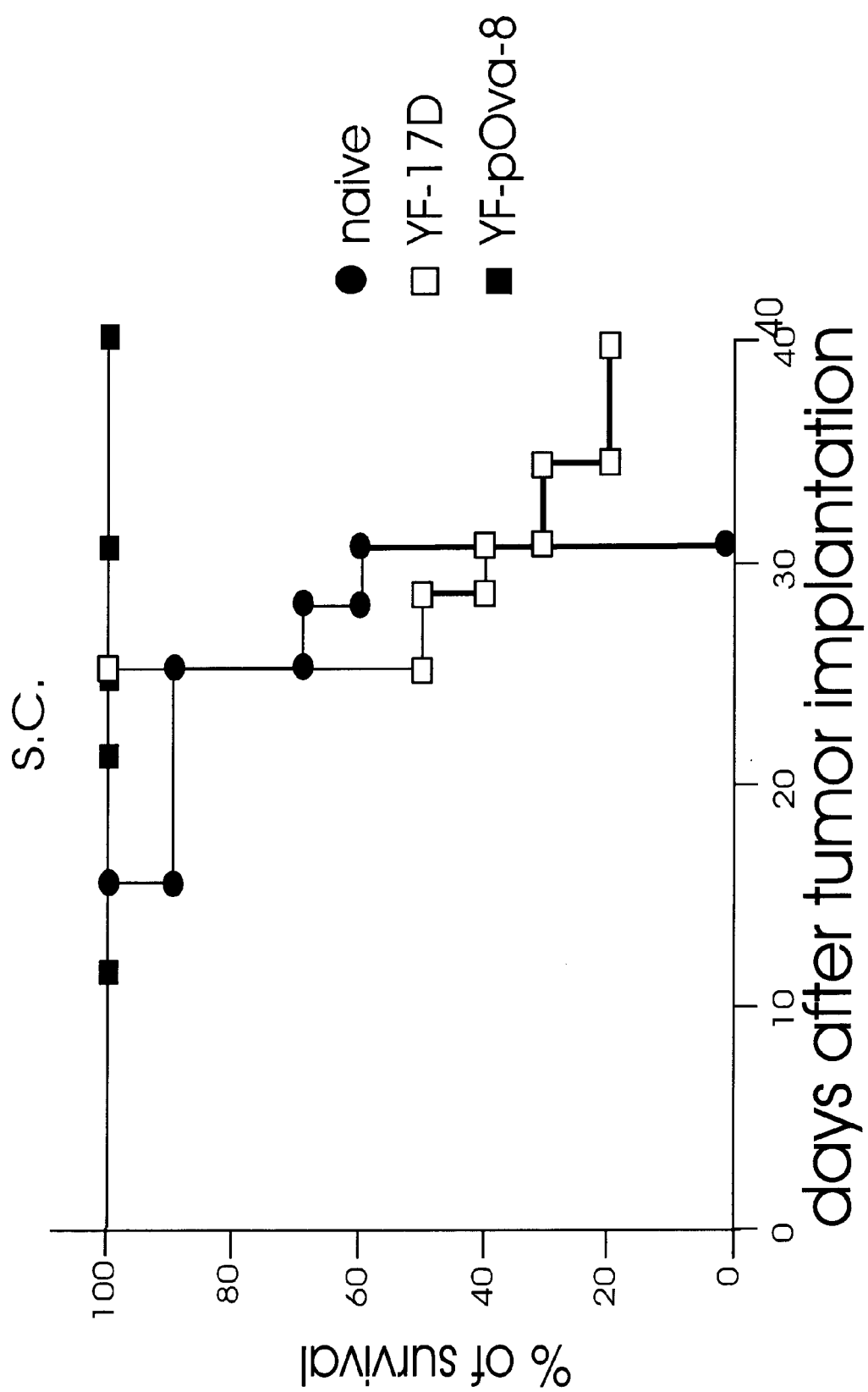
Figure 5D:
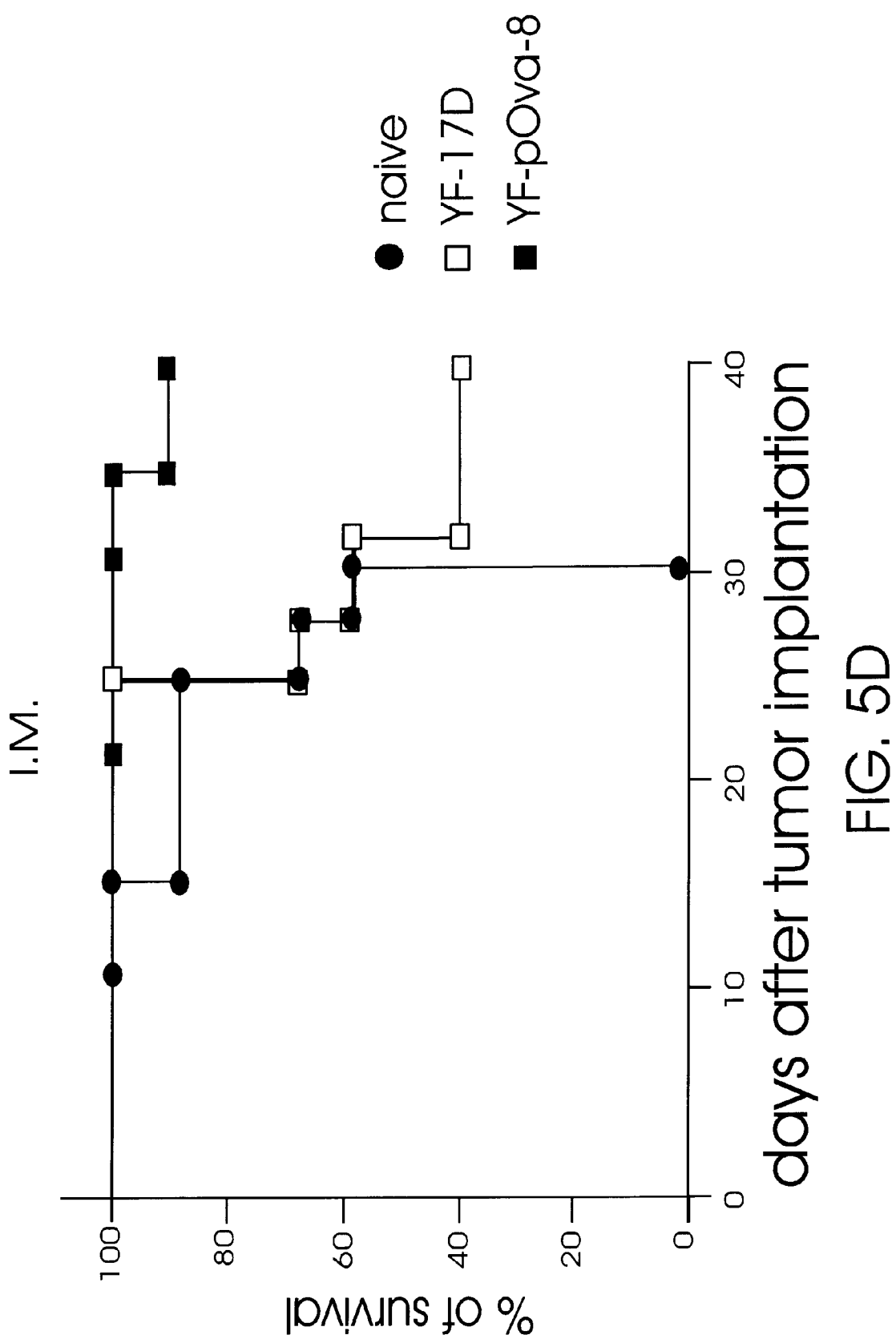
Figure 6A:
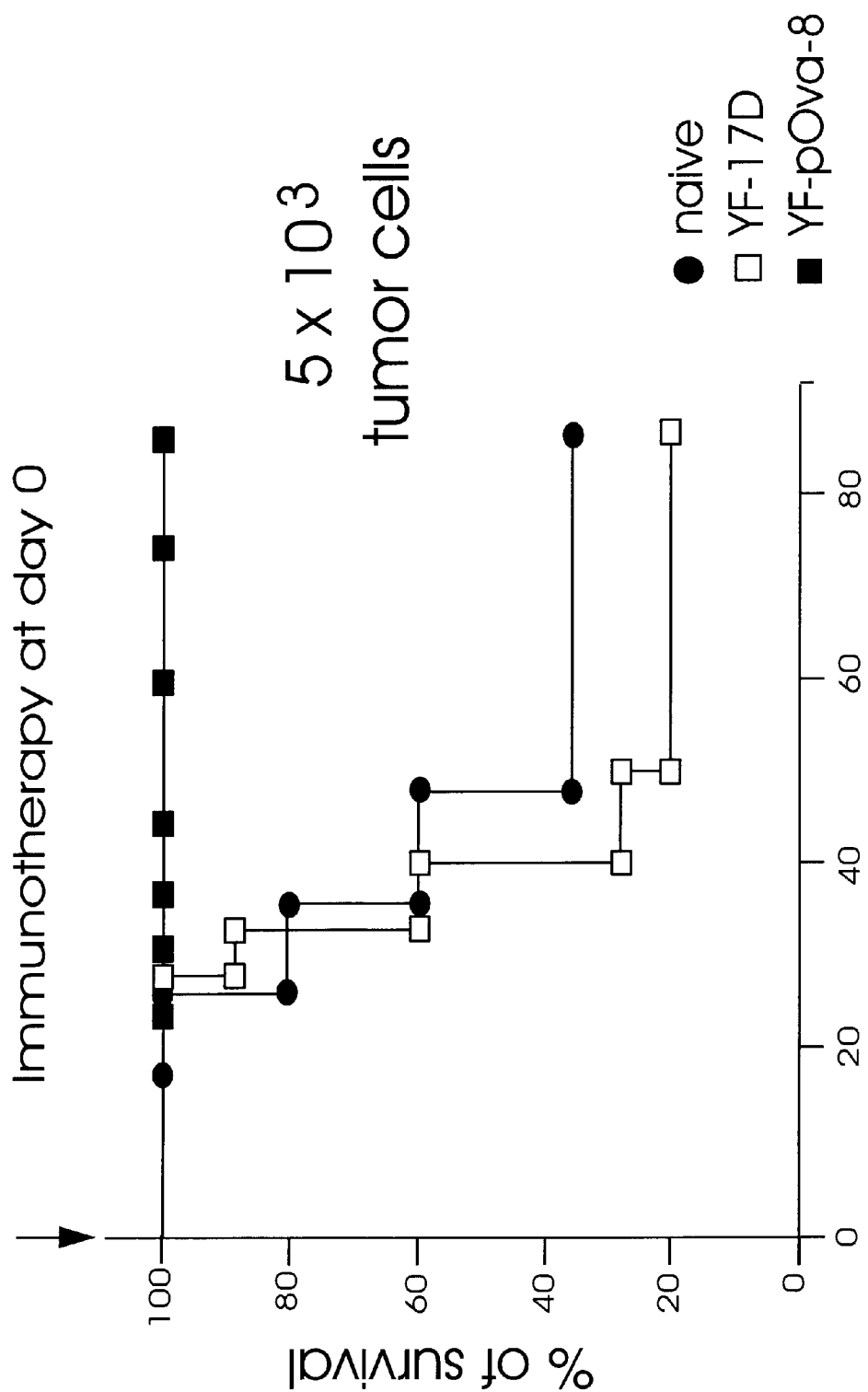
FIGS. 6A–F depict the results of inoculating mice having established B 16 with YF-pOva-8. C57BL/6 mice were injected subcutaneously with melanoma B16-Ova ($5 \times 10^3$ cells/mouse (FIGS. 6A–6C) or $1 \times 10^4$ cells/mouse (FIGS. 6D–6F) at day 0 (tumor implantation). Animals received three subcutaneous inoculations every three days of either PBS (naive) (closed circles), parental 17D (YF-17D) (open squares) or YF-pOva-8 ($4 \times 10^5$ pfu/mouse) (closed squares). Vaccines were administered at the day of tumor implantation (day 0, FIGS. 6A and 6D), five days (day 5, FIGS. 6B and 6E) or ten days (day 10, FIGS. 6C and 6F) after tumor inoculation. Mice were monitored for evidence of tumor growth by palpation and inspection twice a week.
Figure 6B:
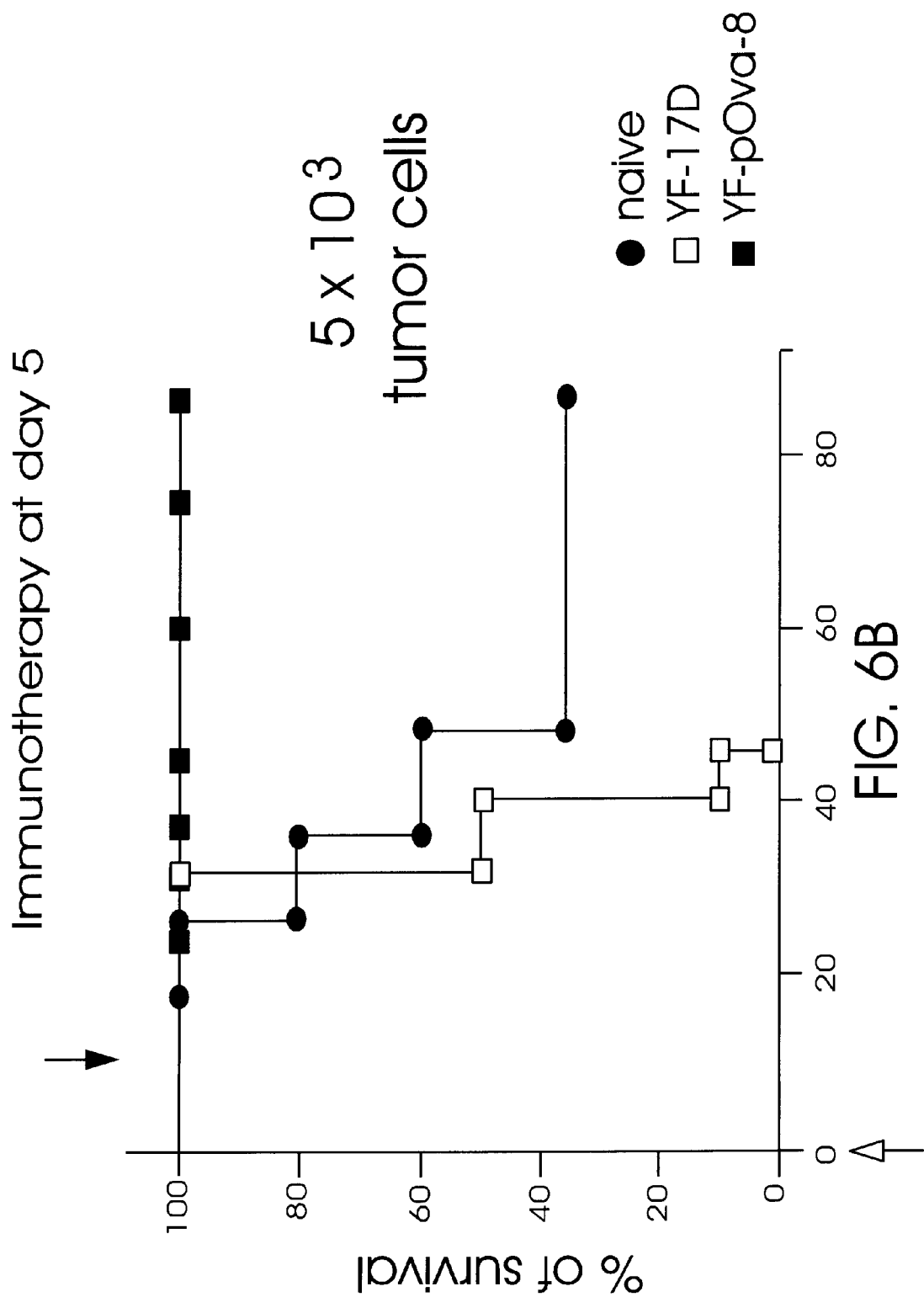
Figure 6C:
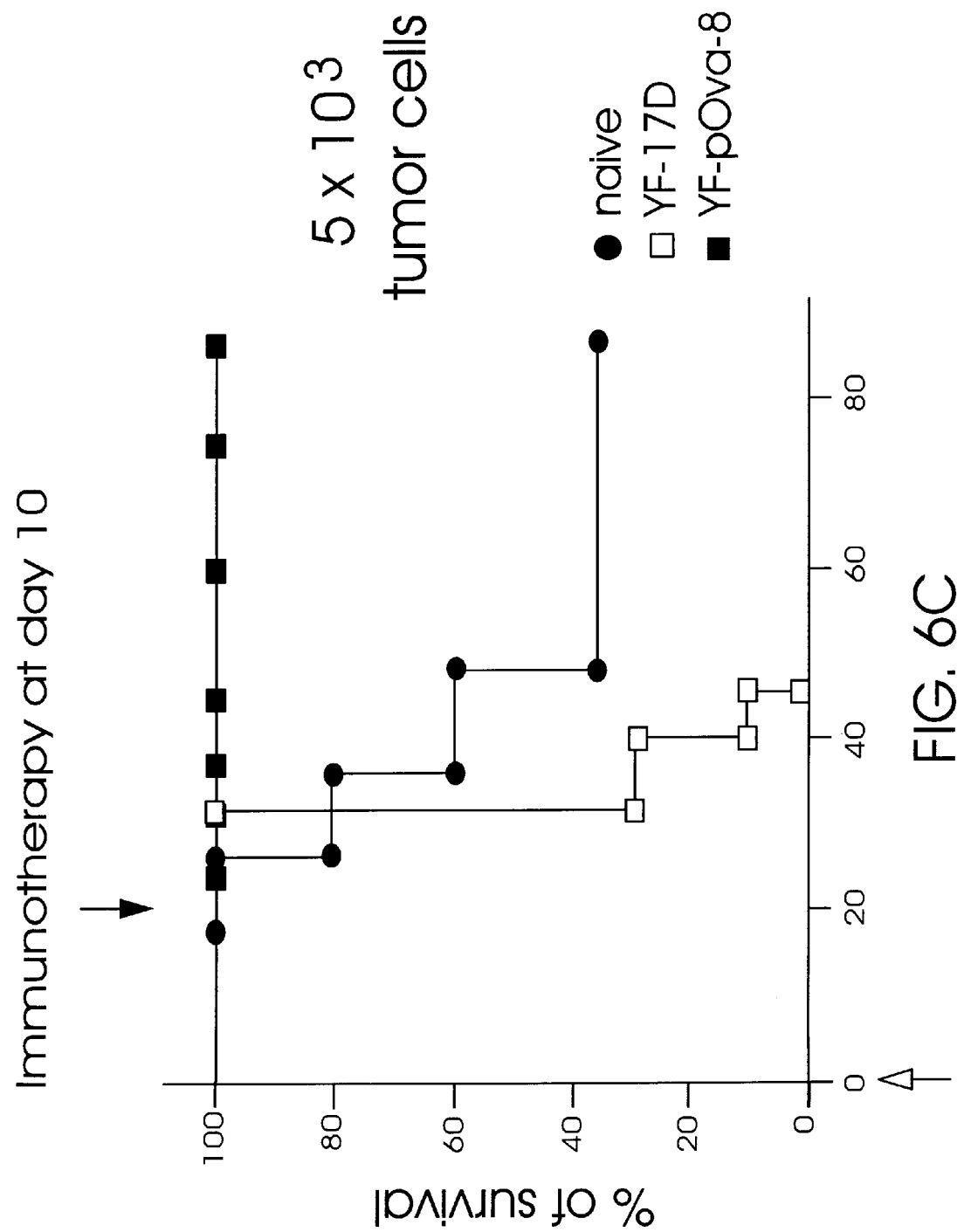
Figure 6D:
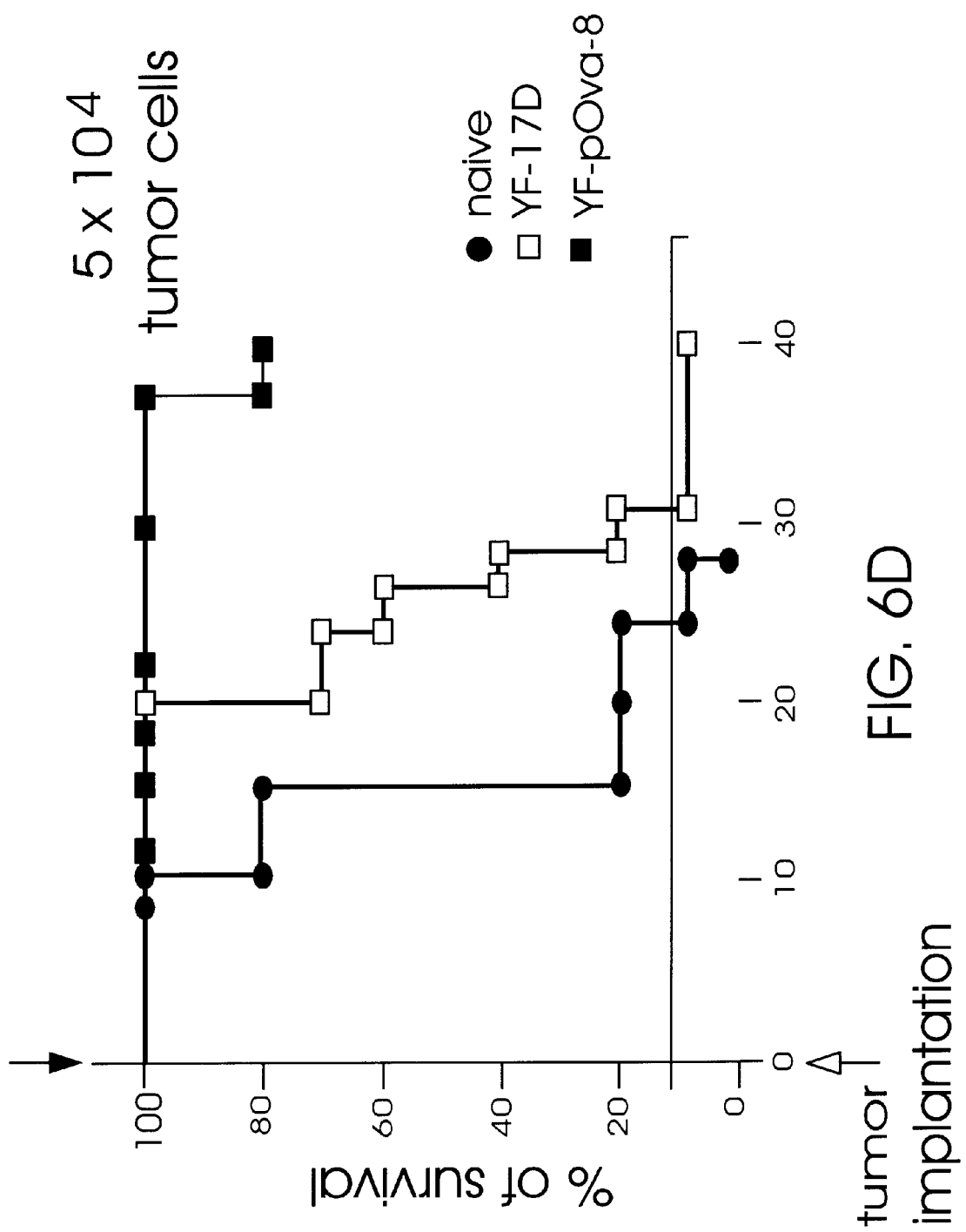
Figure 6E:
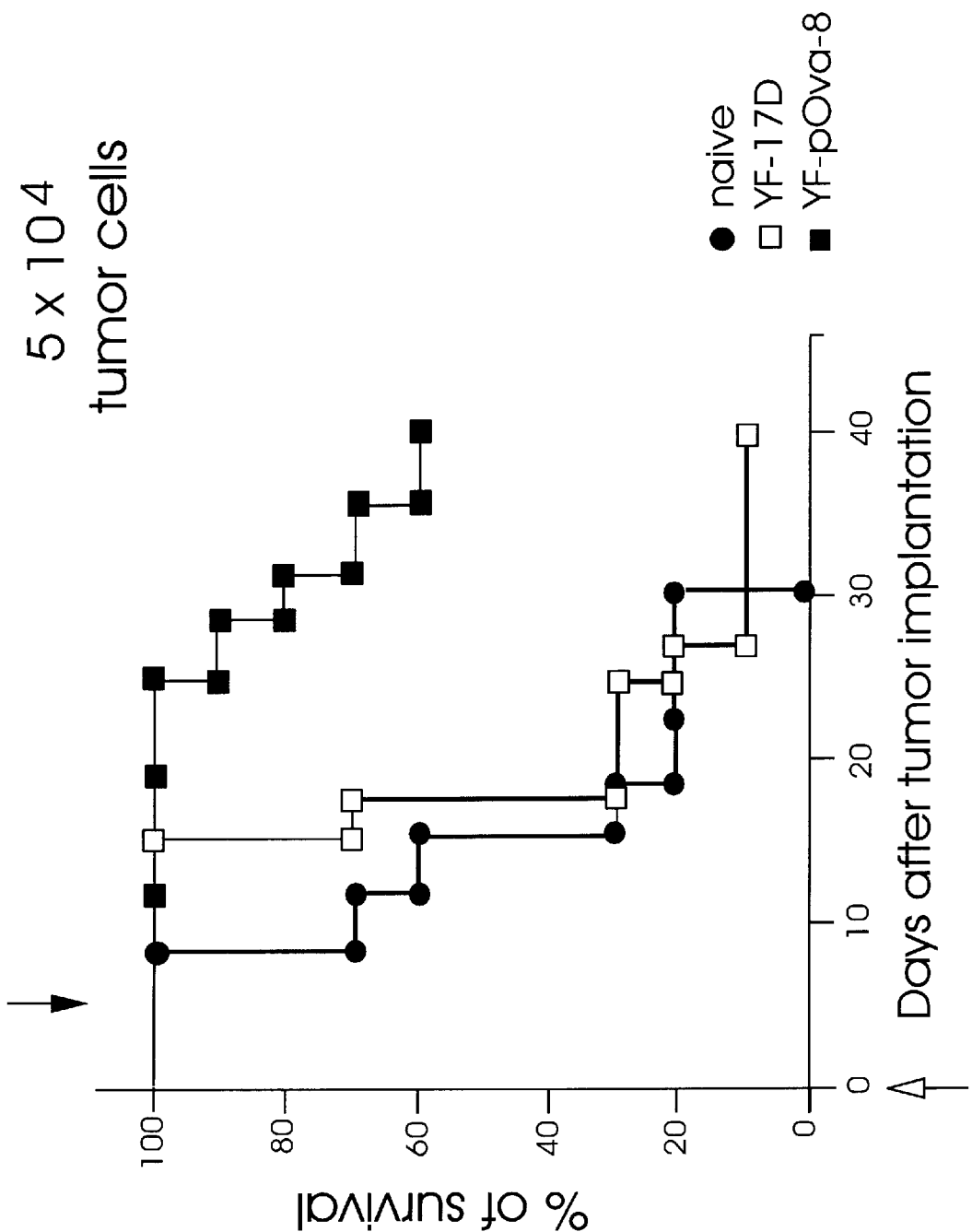
Figure 6F:
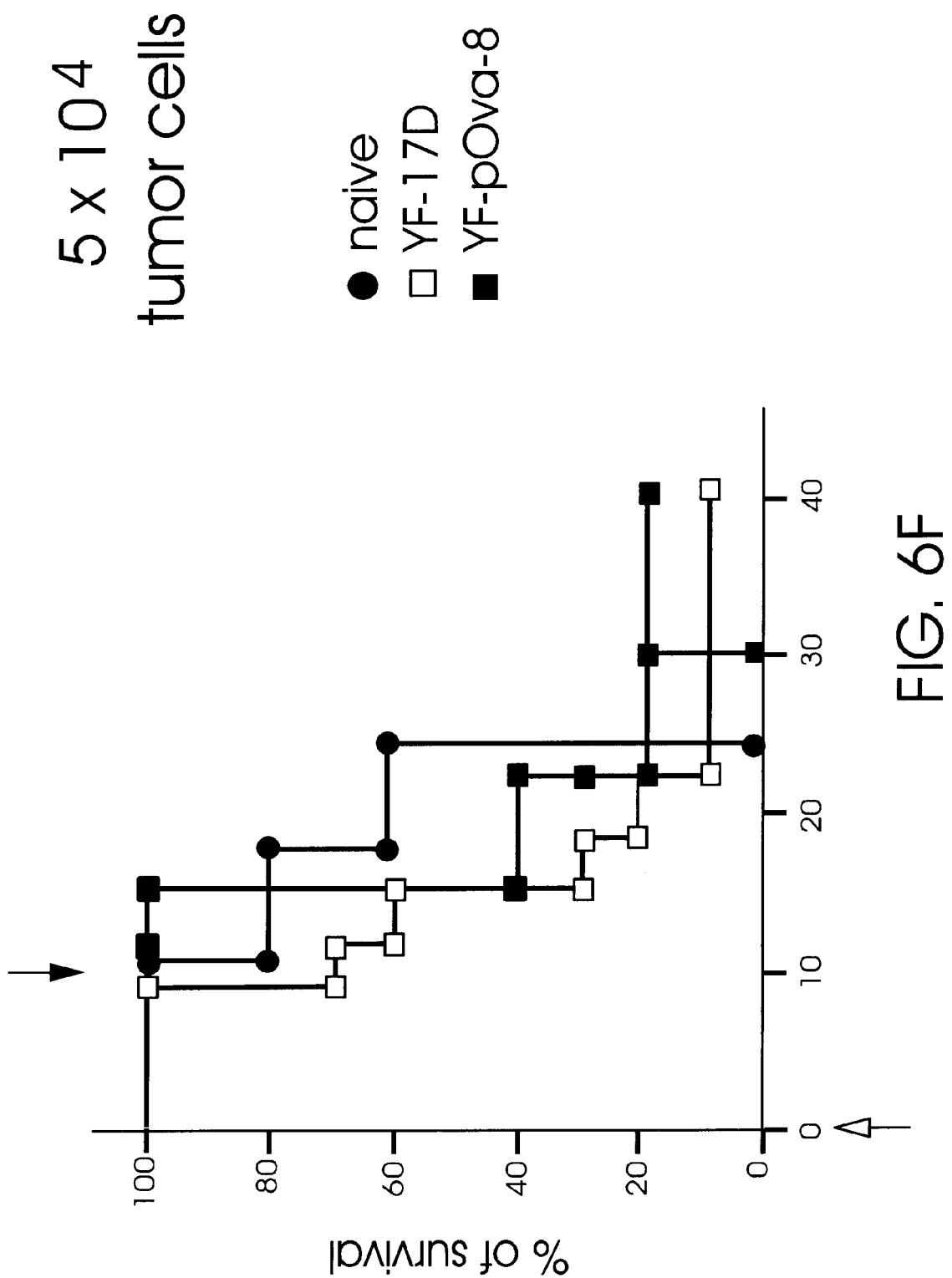

To determine whether recombinant yellow fever viruses are able to induce specific CD8$^+$ T-lymphocytes, mice were inoculated with either YF-pOva-8, parental YF-17D, or PBS (naive). Splenocytes obtained from immunized mice were monitored for the development of a CD8$^-$ T-lymphocyte population that bound MHC class I-SIINFEKL tetramers (FIGS. 3A–3C). Splenocytes from naive mice, or mice immunized with YF-17D, failed to produce SIINFEKL specific T-cells. Both freshly isolated splenocytes and in vitro restimulated splenocytes from YF-pOva-8 immunized mice were assessed for tetrameric binding. Freshly isolated lymphocytes showed minimal tetramer binding after one inoculation (0.5 % of CD8$^-$ T-cells). However, after in vitro stimulation a significant percentage of CD8$^+$ T-cells (8.75%) obtained from mice immunized with YF-pOva-8 were specific for SIINFEKL.

Protective immunity in vivo. To evaluate whether the vector induces protective CTL immunity, we used an established tumor model in which CTLs play an essential role in protecting the host from challenge with a lethal dose of malignant melanoma cells (1). Mice were immunized twice with YF-pOva-8 or YF-17D and then challenged thirty days later with one of two C57BL/6 derived melanomas: the parental B16-F0 tumor cell line, or B16-Ova Which stably expresses chicken ovalbumin. Subcutaneous inoculation of naive mice with B16-Ova cells or parental B16-F0 melanoma cells yielded tumors that grew with similar kinetics and killed naive animals in a few weeks (FIGS. 4A–4D and 5A–5D, data only shown for B16-Ova). Immunization with YF-pOva-8 protected animals against a B16-Ova challenge with a dose 10 times the LD$_{50}$. Immunization protected mice from local tumor growth (FIGS. 4A–4D) and also from death (FIGS. 5A–D).

We administered the recombinant YF-pOva-8 by four different routes—subcutaneous (s.c.), intramuscular (i.m.), intraperitoneal (i.p.) and intravenous (i.v.)—to compare the efficiency of the protective immune response. Subcutaneous and intravenous inoculation elicited potent responses. All of the animals vaccinated with YF-pOva-8 were protected at the time when 100% of the control mice had died. Intraperitoneal and intramuscular inoculations were slightly less efficient; in these groups 10 to 20% of the mice developed tumors and died. The vaccine effect was specific for SIINFEKL because mice vaccinated with YF-pOva-8 were not protected against challenge with parental B16 melanoma cells, which do not express Ova (data not shown). However, we observed a slight, although not significant, delay in tumor growth in mice inoculated with YF-17D when the virus was administered intraperitoneally, subcutaneously or intramuscularly. This effect may be due to increased cytokine production or other immunological responses induced by yellow fever replication. This is not inconsistent with the literature since it has been shown previously, that IFN-γ and IFN-α have anti-tumor and anti-cellular activities on B16 melanoma cells (28–30).

Active immunotherapy of established tumors. Next, we determined whether vaccination with YF recombinant is able to induce regression of established tumors. Mice were inoculated subcutaneously with either $5\times10^3$ or $5\times10^4$ B16-Ova tumor cells and subsequently infected with YF-pOva-8 at the day of tumor implantation (day 0), five days post tumor implantation (day 5) or ten days post tumor implantation (day 10). Mice inoculated with the lower number of B 16-Ova tumor cells ($5\times10^3$), produced tumors in about 60% of unvaccinated mice and were completely protected by vaccination, even if treatment was started 10 days after tumor implantation (FIGS. 6A–6F). For animals inoculated with the higher doses of tumor cells ($5\times10^4$), eighty percent of the animals vaccinated with YF-pOva-8 at day 0 remained tumor-free 45 days after tumor injection, while those injected with parental YF-17D or saline developed tumors and died within 3–4 weeks (FIGS. 6A–6F). Vaccination with YF-17D slightly delayed tumor growth relative to saline, but the effect was minimal and 90% of the animals developed tumors 30 days after tumor implantation. Vaccination with recombinant YF-pOva-8 five days post-tumor implantation resulted in a partial protection (60% of the mice remained tumor-free). Vaccination at day ten had little or no effect on tumor growth. These results demonstrate that treatment of established tumors can be achieved by vaccination with yellow fever recombinants.

Figure 7:
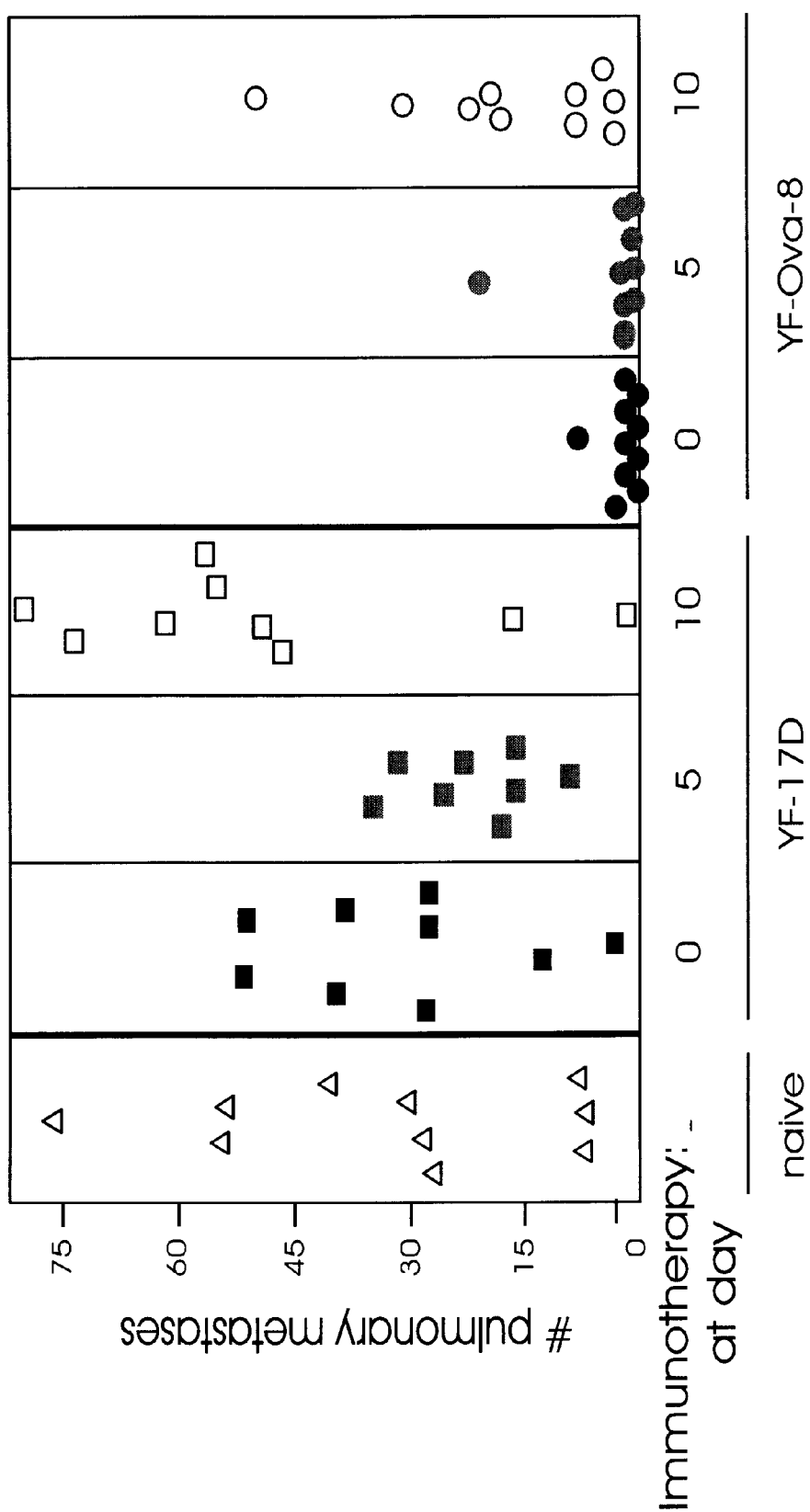
FIG. 7 depicts the lungs of treated mice evaluated in a coded, blinded manner for pulmonary metastases 30 days after the tumor inoculation. The number of pulmonary metastases is shown for individual mice.
Figure 8:
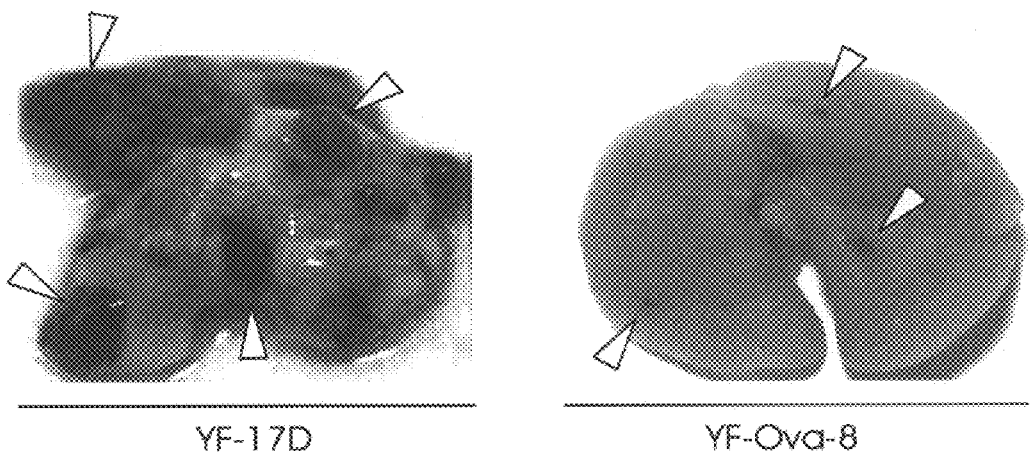
FIG. 8 depicts pictures of lungs treated with YF-pOva-8 or YF-17D at day 30 after tumor inoculation.
Figure 9B:
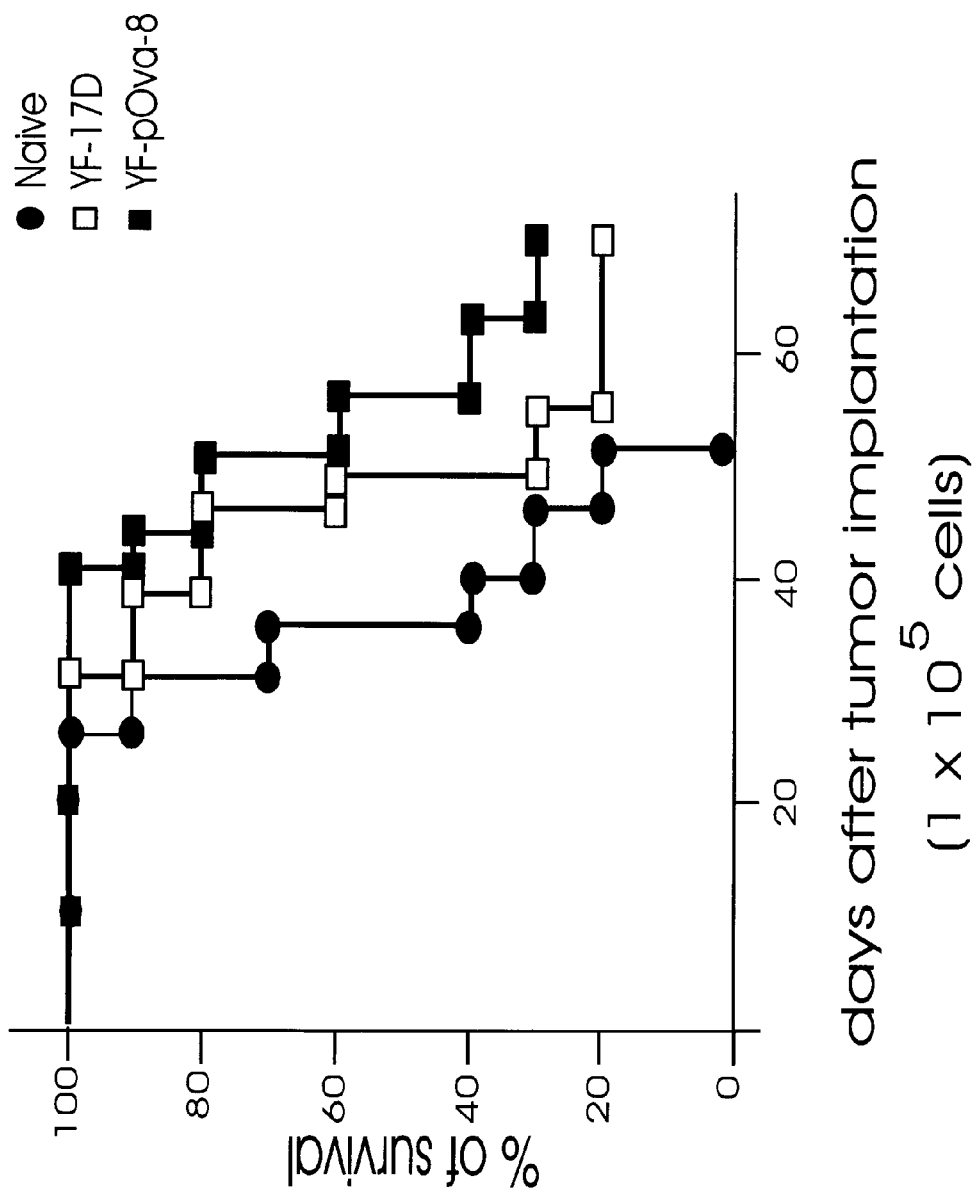

Active immunotherapy of pulmonary metastasis. B16 melanoma cells, when injected into the tail vein of syngenic mice, reproducibly metastasize to the lungs (31). This provides a model to evaluate whether yellow fever recombinants are able to elicit effective anti-metastatic responses. Mice were inoculated intravenously with either $5\times10^4$ or $1\times10^5$ B16-Ova cells, and at day 0, 5 or 10 post-tumor inoculation animals were vaccinated subcutaneously with YF-pOva-8 or control virus. Treatment with the vector prevented death (FIGS. 9A–9B) and substantially reduced both the size and number of lung metastasis (FIGS. 7 and 8). Ten weeks after tumor implantation of $5\times10^4$ cells, 100% of the animals vaccinated at day 0 were healthy (FIGS. 9A–9B). Protection dropped to 80% when vaccination was started at day 5, and dropped further to 20 % when animals were vaccinated starting at day 10 (data not shown). Inoculation with YF- I 7D had no protective effect, and metastases developed with the same kinetics as in animals inoculated with saline (FIGS. 7 and 8). When mice were inoculated with $1 \times 10^5$ tumor cells, only 40% of mice treated at day 0 were protected. These results underline the importance of starting immunotherapy when the tumor burden is low. Nonetheless, these results indicate that recombinant yellow fever viruses expressing a single antigenic epitope are able to elicit a therapeutic anti-tumor response in mice.

While the present invention has been described with reference to the specific embodiments thereof, it should be understood by those skilled in the art that various changes may be made and equivalents may be substituted without departing from the true-spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

BIBLIOGRAPHY

1. Falo L. D., Jr., M. Kovacsovics-Bankowski, K. Thompson, and K. L. Rock. 1995. Targeting antigen into the phagocytic pathway in vivo induces protective tumour immunity. *Nat Med.* 1:649–653.
2. Kawakami, Y., S. Eliyahu, C. H. Delgado, P. F. Robbins, K. Sakaguchi, E. Appella, J. R. Yannelli, G. J. Adema, T. Miki, and S. A. Rosenberg. 1994. Identification of a human melanoma antigen recognized by tumor-infiltrating lymphocytes associated with in vivo tumor rejection. *Proc Natl Acad Sci U S A.* 91:6458–6462.
3. Kawakami, Y., S. Eliyahu, C. H. Delgado, P. F. Robbins, L. Rivoltini, S. L. Topalian, T. Miki, and S. A. Rosenberg. 1994. Cloning of the gene coding for a shared human melanoma antigen recognized by autologous T cells infiltrating into tumor. *Proc Natl Acad Sci U S A.* 91:3515–3519.
4. Rosenberg, S. A., J. R. Yannelli, J. C. Yang, S. L. Topalian, D. J. Schwartzentruber, J. S. Weber, D. R. Parkinson, C. A. Seipp, J. H. Eirihorn, and D. E. White. 1994. Treatment of patients with metastatic melanoma with autologous tumor-infiltrating lymphocytes and interleukin 2. *J Natl Cancer Inst.* 86:1159–1166.
5. Boon, T., E. De Plaen, C. Lurquin, B. Van den Eynde, P. van der Bruggen, C. Traversari, A. Amar-Costesec, and A. Van Pel. 1992. Identification of tumour rejection antigens recognized by T lymphocytes. *Cancer Surv.* 13:23–37.
6. Boon, T. 1993. Tumor antigens recognized by cytolytic T lymphocytes: present perspectives for specific immunotherapy. *Int J Cancer.* 54:177–180.
7. Mandl, S., L. J. Sigal, K. L. Rock, and R. Andino. 1998. Poliovirus vaccine vectors elicit antigen-specific cytotoxic, T cells and protect mice against lethal challenge with malignant melanoma cells expressing a model antigen. *Proc Natl Acad Sci U S A.* 95:8216–8221.
8. Chen, P. W., M. Wang, V. Bronte, Y. Zhai, S. A. Rosenberg, and N. P. Restifo. 1996. Therapeutic antitumor response after immunization with a recombinant. adenovirus encoding a model tumor-associated antigen. *J Immunol.* 156:224–231.
9. Restifo, N. P. 1996. The new vaccines: building viruses that elicit antitumor immunity. *Curr Opin Immunol.* 8:658–663.
10. Carroll, M. W., W. W. Overwijk, R. S. Chamberlain, S. A. Rosenberg, B. Moss, and N. P. Restifo. 1997. Highly attenuated modified vaccinia virus Ankara (MVA) as an effective recombinant vector: a murine tumor model. *Vaccine.* 15:387–394.
11. Rooney, J. F., C. Wohlenberg, K. J. Cremer, B. Moss, and A. L. Notkins. 1988. Immunization with a vaccinia virus recombinant expressing herpes simplex virus type 1 glycoprotein D: long-term protection and effect of revaccination. *J Virol.* 62:1530–1534.
12. Reinhardt, B., R. Jaspert, M. Niedrig, C. Kostner, and J. L'Age-Stehr. 1998. Development of viremia and humoral and cellular parameters of immune activation after vaccination with yellow fever virus strain 17D: a model of human flavivirus infection. *J Med Virol.* 56:159–167.
13. Poland, J. D., C. H. Calisher, T. P. Monath, W. G. Downs, and K. Murphy. 1981. Persistence of neutralizing antibody 30–35 years after immunization with 17D yellow fever vaccine. *Bull World Health Organ.* 59:895–900.
14. Xie, H., A. R. Cass, and A. D. Barrett. 1998. Yellow fever 17D vaccine virus isolated from healthy vaccinees accumulates very few mutations. *Virus Res.* 55:93–99.
15. 1966. Fatal viral encephalitis following 17D yellow fever vaccine inoculation. Report of a case in a 3-year-old child. *Jama.* 198:671–672.
16. Westaway, E. G., 1987. Flavivirus replication strategy. *Adv Virus Res.* 33:45–90.
17. Amberger, V. R., P. A. Paganetti, H. Seulberger, J. A. Eldering, and M. E. Schwab. 1994. Characterization of a membrane-bound metalloendoprotease of rat C6 glioblastoma cells. *Cancer Res.* 54:4017–4025.
18. Chambers, T. J., R. C. Weir, A. Grakoui, D. W. McCourt, J. F. Bazan, R. J. Fletterick, and C. M. Rice. 1990. Evidence that the N-terminal domain of nonstructural protein NS3 from yellow fever virus is a serine protease responsible for site-specific cleavages in the viral polyprotein. *Proc Natl Acad Sci U S A.* 87:8898–8902.
19. Chambers, T. J., A. Grakoui, and C. M. Rice. 1991. Processing of the yellow fever virus nonstructural polyprotein: a catalytically active NS3 proteinase domain and NS2B are required for cleavages at dibasic sites. *J Virol.* 65:6042–6050.
20. Rice, C. M., A. Grakoui, R. Galler, and T. J. Chambers. 1989. Transcription of infectious yellow fever RNA from full-length cDNA templates produced by in vitro ligation. *New Biol.* 1:285–296.
21. Chomczynski, P., and N. Sacchi. 1987. Single-step method of RNA isolation by acid guanidinium thiocyanate-phenol-chloroform extraction. *Anal Biochem.* 162:156–159.
22. Karttunen, J., S. Sanderson, and N. Shastri. 1992. Detection of rare antigen-presenting cells by the lacZ T-cell activation assay suggests an expression cloning strategy for T-cell antigens. *Proc Natl Acad Sci USA.* 89:6020–6024.
23. Altman, J. D., P. A. H. Moss, P. J. R. Goulder, D. H. Barouch, M. G. McHeyzer-Williams, J. I. Bell, A. J. McMichael, and M. M. Davis. 1996. Phenotypic analysis of antigen-specific T lymphocytes [published erratum appears in Science 1998 June 19;280(5371):1821]. *Science.* 274:94–96.
24. Andino, R., D. Silvera, S. D. Suggett, P. L. Achacoso, C. J. Miller, D. Baltimore, and M. B. Feinberg. 1994. Engineering poliovirus as a vaccine vector for the expression of diverse antigens. *Science.* 265:1448–1451.
25. Rotzschke, O., K. Falk, K. Deres, H. Schild, M. Norda, J. Metzger, G. Jung, and H. G. Rammensee. 1990. Isola- 25. tion and analysis of naturally processed viral peptides as recognized by cytotoxic T cells [see comments]. *Nature.* 348:252–254.
26. Mueller, S., and E. Wimmer. 1998. Expression of foreign proteins by poliovirus polyprotein fusion: analysis of genetic stability reveals rapid deletions and formation of cardioviruslike open reading frames. *J Virol.* 72:20–31.
27. Tang, R. S., D. J. Barton, J. B. Flanegan, and K. Kirkegaard. 1997. Poliovirus RNA recombination in cell-free extracts. *Rna.* 3:624–633.
28. Arany, I., C. M. Fleischmann, S. K. Tyring, and W. R. Fleischmann. 1997. Interferon regulates expression of mda-6/WAF1/CIP1 and cyclin-dependent kinases independently from p53 in B16 murine melanoma cells. *Biochem Biophys Res Commun.* 233:678–680.
29. Arany, I., C. M. Fleischmann, S. K. Tyring, and W. R. Fleischmann, Jr. 1997. Lack of mda-6/WAF1/CIP1-mediated inhibition of cyclin-dependent kinases in interferon-alpha resistant murine B16 melanoma cells. *Cancer Lett.* 119:237–240.
30. Lasek, W., A. Wankowicz, K. Kuc, W. Feleszko, J. Golab, A. Giennasz, W. Wiktor-Jedrzejczak, and M. Jakobisiak. 1995. Potentiation of antitumor effects of tumor necrosis factor alpha and interferon gamma by macrophage-colony-stimulating factor in a MmB16 melanoma model in mice. *Cancer Immunol Immunother.* 40:315–321.
31. Poste, G., and I. J. Fidler. 1980. The pathogenesis of cancer metastasis. *Nature.* 283:139–146.
32. Lu, H., L. Alexander, and E. Wimmer. 1995. Construction and genetic analysis od dicistronic polioviruses containing open reading frame for epitopes of human Immunodeficiency virus type 1 gp120. *J. Virol.* 69:4797–4806.
33. Burke, K. L., J. W. Almond, and D. J. Evans. 1991. Antigen chimeras of poliovirus. *Prog Med Virol.* 38:56–68.
34. Alexander, L., H. H. Lu, M. Gromeier, and E. Wimmer. 1994. Dicistronic polioviruses as expression vectors for foreign genes. *Aids Res Hum Retroviruses.* 10 Suppl 2:S57–60.
35. Monath, T. P., and A. Nasidi. 1993. Should yellow fever vaccine be included in the expanded program of immunization in Africa? A cost-effectiveness analysis for Nigeria. *Am J Trop Med Hyg.* 48:274–299.
36. Monath, T. P. 1990. Flaviviruses. In Virology. B. N. Fields, and D. M. Knipe, editors. Raven Press, Ltd., New York. 763–814.
37. Monath, T. P. 1991. Yellow fever: Victor, Victoria? Conqueror, conquest? Epidemics and research in the last forty years and prospects for the future. *Am J Trop Med Hyg.* 45:1–43.
38. Khromykh, A. A., and E. G., Westaway. 1997. Subgenomic replicons of the flavivirus Kunjin: construction and applications. *J Virol.* 71:1497–1505.
39. Vamavski, A. N., and A. A. Khromykh. 1999. Noncytopathic flavivirus replicon RNA-based system for expression and delivery of heterologous genes: *Virology.* 255:366–375.
40. Chambers, T. J., A. Nestorowicz, P. W. Mason, and C. M. Rice. 1999. Yellow fever/Japanese encephalitis chimeric viruses: construction and biological properties. *J Virol.* 73:3095–3101.
41. Guirakhoo, F., Z. X. Zhang, T. J. Chambers, S. Delagrave, J. Arroyo, A. D. Barrett, and T. P. Monath. 1999. Immunogenicity, genetic stability, and protective efficacy of a recombinant, chimeric yellow fever-Japanese encephalitis virus (Chimeri Vax-JE) as a live, attenuated vaccine candidate against Japanese encephalitis. *Virology.* 257:363–372.
42. Monath, T. P., K. Soike, I. Levenbook, Z. X. Zhang, J. Arroyo, S. Delagrave, G. Myers, A. D. Barrett, R. E. Shope, M. Ratterree, T. J. Chambers, and F. Guirakhoo. 1999. Recombinant, chimaeric live, attenuated vaccine (ChimeriVax) incorporating the envelope genes of Japanese encephalitis (SA14-14-2) virus and the capsid and nonstructural genes of yellow fever (17D) virus is safe, immunogenic and protective in non-human primates. *Vaccine.* 17:1869–1882.
43. Bohm, W., S. Thoma, F. Leithauser, P. Moller, R. Schirmbeck, and J. Reimann. 1998. T cell-mediated, IFN-gamma-facilitated rejection of murine B16 melanomas. *J Immunol.* 161:897–908.
44. Simons, J. W., E. M. Jaffee, C. E. Weber, H. I. Levitsky, W. G. Nelson, M. A. Carducci, A. J. Lazenby, L. K. Cohen, C. C. Finn, S. M. Clift, K. M. Hauda, L. A. Beck, K. M. Leiferman, A. H. Owens, Jr., S. Piantadosi, G. Dranoff, R. C. Mulligan, D. M. Pardoll, and F. F. Marshall. 1997. Bioactivity of autologous irradiated renal cell carcinoma vaccines generated by ex vivo granulocyte-macrophage colony-stimulating factor gene transfer. *Cancer Res.* 57:1537–1546.
45. Ellem, K. A., M. G. O'Rourke, G. R. Johnson, G. Parry I. S. Misko, C. W. Schmidt, P. G. Parsons, S. R. Burrows, S. Cross, A. Fell, C. L. Li, J. R. Bell, P. J. Dubois, D. J. Moss, M. F. Good, A. Kelso, L. K. Cohen, G. Dranoff, and R. C. Mulligan. 1997. A case report: immune responses and clinical course of the first human use of granulocyte/macrophage-colony-stimulating-factor-transduced autologous melanoma cells for immunotherapy. *Cancer Immunol Immunother.* 44:10–20.
46. Dranoff, G., R. Soiffer, T. Lynch, M. Mihm, K. Jung, K. Kolesar, L. Liebster, P. Lam, R. Duda, S. Mentzer, S. Singer, K. Tanabe, R. Johnson, A. Sober, A. Bhan, S. Clift, L. Cohen, G. Parry, J. Rokovich, L. Richards, J. Drayer, A. Berns, and R. C. Mulligan. 1997. A phase I study of vaccination with autologous, irradiated melanoma cells engineered to secrete human granulocyte-macrophage colony stimulating factor. *Hum Gene Ther.* 8:111–123.
47. Dranoff, G., E. Jaffee, A. Lazenby, P. Golumbek, H. Levitsky, K. Brose, V. Jackson, H. Hamada, D. Pardoll, and R. C. Mulligan. 1993. Vaccination with irradiated tumor cells engineered to secrete murine granulocyte-macrophage colony-stimulating factor stimulates potent, specific, and long-lasting anti-tumor immunity. *Proc Natl Acad Sci U S A.* 90:3539–3543.
48. de Zoeten, E. F., V. Carr-Brendel, and E. P. Cohen. 1998. Resistance to melanoma in mice immunized with semiallogeneic fibroblasts transfected with DNA from mouse melanoma cells. *J Immunol.* 160:2915–2922.
49. Yang, S., T. L. Darrow, C. E. Vervaert, and H. F. Seigler. 1997. Immunotherapeutic potential of tumor antigen-pulsed and unpulsed dendritic cells generated from murine bone marrow. *Cell Immunol.* 179:84–95.
50. Kawakami, Y., S. Eliyahu, K. Sakaguchi, P. F. Robbins, L. Rivoltini, J. R. Yannelli, E. Appella, and S. A. Rosenberg. 1994. Identification of the immunodominant peptides of the MART-1 human melanoma antigen recognized by the majority of HLA-A2-restricted tumor infiltrating lymphocytes. *J Exp Med.* 180:347–352.
51. Overwijk, W. W., D. S.. Lee, D. R. Surman, K. R. Irvine, C. E. Touloukian, C. C. Chan, M. W. Carroll, B. Moss, S. A. Rosenberg, and N. P. Restifo. 1999. Vaccination with a recombinant vaccinia virus encoding a "self" antigen induces autoimmune vitiligo and tumor cell destruction in mice: requirement for CD4(+) T lymphocytes. *Proc Natl Acad Sci U S A.* 96:2982–2987.

What is claimed is:

1. An isolated replication-competent recombinant yellow fever virus comprising an insertion of an exogenous nucleic acid sequence encoding an exogenous polypeptide, wherein infection of a host with the recombinant virus provides for expression of the exogenous polypeptide by the host cell and induction of an immune response in a host.

2. The isolated recombinant yellow fever virus of claim 1, wherein the exogenous nucleic acid sequence is expressed as a component of a recombinant viral polyprotein precursor.

3. The isolated recombinant yellow fever virus of claim 2, wherein the recombinant polyprotein precursor comprises a proteolytic cleavage site.

4. The isolated recombinant yellow fever virus of claim 3, wherein the proteolytic cleavage site is positioned to provide for release of the exogenous polypeptide upon proteolytic processing.

5. The isolated recombinant yellow fever virus of claim 1, wherein the exogenous polypeptide is a polypeptide of a virus other than yellow fever virus.

6. The isolated recombinant yellow fever virus of claim 1, wherein the exogenous polypeptide is a polypeptide of a microbial pathogen other than yellow fever virus.

7. The isolated recombinant yellow fever virus of claim 1, wherein the virus is live and attenuated.

8. The isolated recombinant yellow fever virus of claim 1, wherein the exogenous polypeptide is expressed on the surface of the host cell following infection.

9. The isolated recombinant yellow fever virus of claim 1, wherein the exogenous polypeptide is secreted from the host cell following infection.

10. An isolated host cell infected with the recombinant yellow fever virus of claim 1.

11. A composition comprising the recombinant yellow fever virus of claim 1, and a buffer.

12. The composition of claim 11, further comprising a pharmaceutically acceptable excipient.

13. A method of eliciting an immune response in a mammalian host to an antigenic polypeptide, comprising:

administering a recombinant yellow fever virus of claim 1 to a mammalian host, wherein the exogenous polypeptide is an antigenic polypeptide, wherein said administering provides for infection of a host cell and expression of the antigenic polypeptide;

wherein expression of the exogenous polypeptide results in induction of an immune response in the host to the antigenic polypeptide.

14. The method of claim 13, wherein the antigenic polypeptide is a polypeptide of a microbial pathogen.

15. An isolated replication-competent recombinant yellow fever virus comprising a sequence encoding a recombinant polyprotein precursor, the polyprotein precursor comprising an insertion of an exogenous nucleic acid sequence encoding an exogenous polypeptide.

16. The isolated recombinant yellow fever virus of claim 15, wherein the polyprotein precursor comprises a proteolytic cleavage site such that the exogenous polypeptide is released from the recombinant polyprotein precursor upon proteolytic processing.

17. The isolated recombinant yellow fever virus of claim 15, wherein the exogenous polypeptide is a polypeptide of a virus other than yellow fever virus.

18. The isolated recombinant yellow fever virus of claim 15, wherein the virus is live and attenuated.

19. The isolated recombinant yellow fever virus of claim 15, wherein the exogenous polypeptide is expressed on the surface of the host cell following infection.

20. The isolated recombinant yellow fever virus of claim 15, wherein the exogenous polypeptide is secreted from the host cell following infection.

21. An isolated host cell infected with the recombinant yellow fever virus of claim 15.

22. A composition comprising the recombinant yellow fever virus of claim 15, and a buffer.

23. The composition of claim 22, further comprising a pharmaceutically acceptable excipient.

* * * * *

SEQUENCE LISTING

<160> NUMBER OF SEQ ID NOS: 4

<210> SEQ ID NO 1
<211> LENGTH: 8
<212> TYPE: PRT
<213> ORGANISM: Artificial Sequence
<220> FEATURE:
<223> OTHER INFORMATION: exogenous peptide

<400> SEQUENCE: 1

Ser Ile Ile Asn Phe Glu Lys Leu
1               5

<210> SEQ ID NO 2
<211> LENGTH: 55
<212> TYPE: DNA
<213> ORGANISM: Artificial Sequence
<220> FEATURE:
<223> OTHER INFORMATION: synthesized oligonucleotide

<400> SEQUENCE: 2
atcgcggacc gagtggtttt gtgtttgtca tccaaaggtc tgcttattct tgagc        55

<210> SEQ ID NO 3
<211> LENGTH: 24
<212> TYPE: DNA
<213> ORGANISM: Artificial Sequence
<220> FEATURE:
<223> OTHER INFORMATION: synthesized oligonucleotide

<400> SEQUENCE: 3
caatgaggca ctcgcagcag ctgg        24

<210> SEQ ID NO 4
<211> LENGTH: 23
<212> TYPE: DNA
<213> ORGANISM: Artificial Sequence
<220> FEATURE:
<223> OTHER INFORMATION: synthesized oligonucleotide

<400> SEQUENCE: 4
tgccctagct ctgtgcgctg ccc        23